(12) United States Patent
Zhou et al.

(10) Patent No.: US 9,994,566 B2
(45) Date of Patent: Jun. 12, 2018

(54) COMPOUND OF 5-HYDROXYL-1,7-NAPHTHYRIDINE SUBSTITUTED BY ARYL OR HETEROARYL, PREPARATION METHOD THEREOF AND PHARMACEUTICAL USE THEREOF

(71) Applicant: SHENYANG SUNSHINE PHARMACEUTICAL CO. LTD., Shenyang, Liaoning (CN)

(72) Inventors: Yunlong Zhou, Nanjing (CN); Suixiong Cai, San Diego, CA (US); Guangfeng Wang, Shanghai (CN); Lingling Jiao, Taizhou (CN); Ping Min, Shanghai (CN); Yu Jing, Taizhou (CN); Ming Guo, San Diego, CA (US)

(73) Assignee: SHENYANG SUNSHINE PHARMACEUTICAL CO. LTD., Shenyang (CN)

( * ) Notice: Subject to any disclaimer, the term of this patent is extended or adjusted under 35 U.S.C. 154(b) by 0 days. days.

(21) Appl. No.: 15/561,464

(22) PCT Filed: Dec. 14, 2015

(86) PCT No.: PCT/CN2015/097245
§ 371 (c)(1),
(2) Date: Sep. 25, 2017

(87) PCT Pub. No.: WO2016/155358
PCT Pub. Date: Oct. 6, 2016

(65) Prior Publication Data
US 2018/0118738 A1    May 3, 2018

(30) Foreign Application Priority Data

Mar. 27, 2015 (CN) .......................... 2015 1 0141555

(51) Int. Cl.
*C07D 471/04* (2006.01)

(52) U.S. Cl.
CPC ............. *C07D 471/04* (2013.01); *A61P 1/00* (2018.01); *A61P 7/06* (2018.01); *A61P 19/02* (2018.01)

(58) Field of Classification Search
None
See application file for complete search history.

(56) References Cited

U.S. PATENT DOCUMENTS 8,921,389 B2 * 12/2014 Ng ....................... C07D 471/04
514/300

* cited by examiner

*Primary Examiner* — Heidi Reese
(74) *Attorney, Agent, or Firm* — Greer, Burns & Crain, Ltd.

(57) ABSTRACT

Disclosed are a compound of the following formula (I) or a pharmaceutically acceptable salt thereof, a preparation method thereof, pharmaceutical compositions and uses thereof in the preparation of a medicine for inhibiting HIF prolyl hydroxylase or a medicine for promoting the generation of endogenous EPO, wherein in the formula (I), $R_1$ and $R_2$ are each independently hydrogen; $R_3$ is hydrogen or $C_{1-3}$ alkyl; and Ar is an aromatic ring or an heteroaromatic ring selected from a naphthalene ring, a pyridine ring, a thiophene ring, a furan ring and a substituted benzene ring.

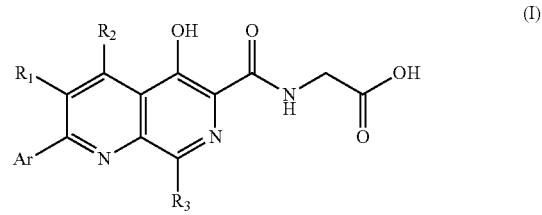

25 Claims, No Drawings

COMPOUND OF 5-HYDROXYL-1,7-NAPHTHYRIDINE SUBSTITUTED BY ARYL OR HETEROARYL, PREPARATION METHOD THEREOF AND PHARMACEUTICAL USE THEREOF

BACKGROUND

The present invention relates to the field of medicine, and particularly to a novel 5-hydroxyl-1,7-naphthyridine compound substituted by aryl or heteroaryl, a preparation method thereof and a pharmaceutical use thereof.

Hypoxia inducible factor (HIF) is a section of transcriptional activator containing basic helix-loop-helix (bHLH) and PAS (Per/Arnt/Sim) that responds to the hypoxia conditions by mediating a series of gene regulation in biological cells. (Chowdhury, R., Hardy, A, Schofield, C. J., The human oxygen sensing machinery and its manipulation, Chem. Soc. Rev., 2008, 37, 1308-1319; Kaelin, W. G., Jr., Ratcliffe, P. J., Oxygen sensing by metazoans: the central role of the HIF hydroxylase pathway, Mol. Cell, 2008, 30, 393-402; Schofield, C. J., Ratcliffe, P. J., Oxygen sensing by HIF hydroxylases, Nat. Rev. Mol. Cell. Biol., 2004, 5, 343-354).

In 1992, during the study of erythropoietin (EPO, an erythropoiesis-stimulating hormone), Wang et al. found the transcriptional activator that stimulates the generation of EPO in hypoxic cells, and thus named it Hypoxia Inducible Factor, abbreviated as HIF. HIF is essential for cellular adaptation and survival to hypoxia, and the experiments show that under the effect of HIF, cells can still survive even if the oxygen content in the cells is reduced to 1% from normal 20%.

HIF consists of two subunits, HIF-α and HIF-β. HIF-α contains an oxygen-dependent degradation domain (abbreviated as ODDD), which is a key element unit in response to cellular oxygen content. HIF-α can form a stable dimer with HIF-β. After this dimer enters the nucleus, it activates the expression of important enzymes or enzyme systems such as glucose metabolism-related enzymes, GLUT-1, erythropoietin and vascular endothelial growth factor (VEGF), and thus resists the cell hypoxia conditions. HIF-β is a type of aryl hydrocarbon nuclear translator (abbreviated as ARNT), which forms a heterodimer with HIF-α to activate transcription of downstream genes.

To date, three HIF-α subtypes have been discovered, HIF-1α, HIF-2α, and HIF-3α, respectively. HIF-1α, first discovered by Wang in 1995, is widely expressed in human and mouse bodies. HIF-2α was isolated and identified in 1997, which has a protein sequence with 48% similarity to that of HIF-1α and therefore has the similar functions to HIF-1α, however, HIF-2α is only expressed in lung, endothelium and carotid artery. HIF-3α is a newly discovered HIF-α subtype, and little research has been done on it yet.

Studies have shown that the expression of HIF-α in cells is not affected by oxygen content, but HIF-α cannot stably exist in the cells having normal oxygen content, and has a half-life of only 5 minutes. HIF-α can only be stable under hypoxic conditions and thus play the normal function of activation of downstream transcription factors. In the cells having normal oxygen content, the prolyl at positions 402, 564 in the ODDD region of HIF-α was oxidized by prolyl hydroxylase to form 4-hydroxyprolyl, so that HIF-α cannot be dimmed with HIF-β, but soon binds to pVHL protein and then be degraded, and therefore cannot play an anti-hypoxia function. Prolyl hydroxylase (also abbreviated as PHD or EGLN), which plays a key role in the degradation of HIF-α, is a 2-oxoglutatone (2-OG)-dependent oxygenase. With 2-OG and divalent iron ions as prosthetic groups, PHD transfers an oxygen atom to the 4-position of the prolyl molecule to form a hydroxyprolyl, and meanwhile converts 2-OG into one carbon dioxide molecule and succinic acid. Both 2-OG analogs and divalent nickel, cobalt and manganese ions can antagonize the oxidation of prolyl in HIF-α by PHD, and inhibit the degradation of HIF-α, so that HIF-α can successfully be dimmed with HIF-β, and thus stimulates the downstream transcription factors, and ultimately plays an anti-hypoxia function. Studies have found that PHD has three subtypes: PHD1, PHD2, and PHD3. Further studies suggest that inhibition on PHD1 can help to treat skeletal muscle cell degradation, can protect myofibroblasts under ischemic conditions, treat inflammatory enteritis and colitis, and treat heart failure and ischemia in patients with heart disease and kidney disease. However, no study has shown that the other two PHD subtypes have difference in functions.

One of the important roles of HIF is to activate the expression of erythropoietin (EPO) in living organisms. As a glycoprotein hormone, EPO can stimulate red blood cell proliferation, differentiation and maturation. EPO on the one hand can stimulate bone marrow hematopoietic function, timely and effectively increase the number of red blood cells, thereby enhancing the oxygen carrying capacity of the blood. On the other hand, EPO can enhance the body's oxygen binding, transport and supply capacity, and improve hypoxia conditions. Under normal physiological conditions, EPO is mainly synthesized and secreted by the kidney, therefore, a patient with kidney failure will suffer from ischemia because EPO cannot be normally synthesized in the body. In the late 1980s, Amgen company first successfully achieved industrialization of EPO and gradually applied EPO to the patients with anemia caused by chronic kidney failure, AIDS, cancer and chemotherapy. However, with the huge development of EPO generation and application, exogenous EPO administration still faces several problems: 1, EPO is expensive, and is a great burden especially for the patients who need long-term use. 2, as a macromolecule glycoprotein, EPO also has the characteristics of low bioavailability, short half-life in the organism, easy to be hydrolyzed by the enzyme in the gastrointestinal tract, so EPO must be frequently administrated by injection, which limits the probability of patient's self-administration, and brings great inconvenience to the patients. 3, Industrially synthetic EPO still cannot avoid the immunogenicity and the product has certain medication risks.

Due to these problems in the use of exogenous macromolecule EPO, it will be very promising to replace exogenous EPO and bring the patients more choices by developing small molecule HIF prolyl hydroxylase inhibitors to inhibit the HIF-α degradation, thereby stimulating the generation of endogenous EPO in human body.

So far, two HIF prolyl hydroxylases, Akebia's AKB-6548 and Fibrogen's FG-4592, have been introduced into the clinical phase II study. (Refer to WO 2012170377A1, US2010331374A1, US2010305097A1, US2007299086A1, US2004254215A1, US2007298104A1, US2009082357A1, US2010113444A1, WO2013134660, WO2010059552A1).

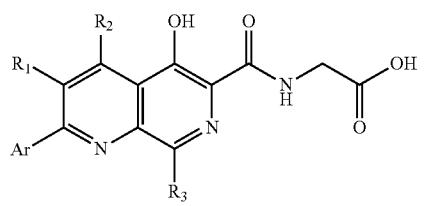

AKB-6548

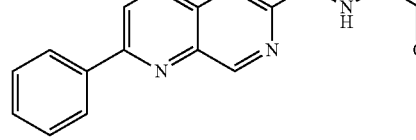

FG-4592

SUMMARY

It is an object of the present invention to provide a 5-hydroxyl-1,7-naphthyridine compound substituted by aryl or heteroaryl or a salt thereof for inhibiting HIF prolyl hydroxylase.

It is another object of the present invention to provide a method for preparing the above compound.

It is another object of the present invention to provide a pharmaceutical composition comprising the above compound or a salt thereof.

It is a further object of the present invention to provide a use of the above compound or a salt thereof in preparation of a medicament.

The objects of the present invention are achieved by the following solutions:

A compound having the following formula (I) or a pharmaceutically acceptable salt thereof:

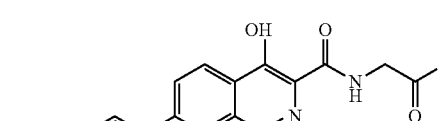
(I)

wherein, $R_1$, $R_2$ are each independently hydrogen;

$R_3$ is hydrogen or $C_{1-3}$ alkyl;

Ar is an aromatic ring or an aromatic heterocyclic ring selected from the group consisting of a naphthalene ring, a pyridine ring, a thiophene ring, a furan ring and a substituted benzene ring.

When Ar is a substituted benzene ring, the compound of the present invention has the following formula (II):

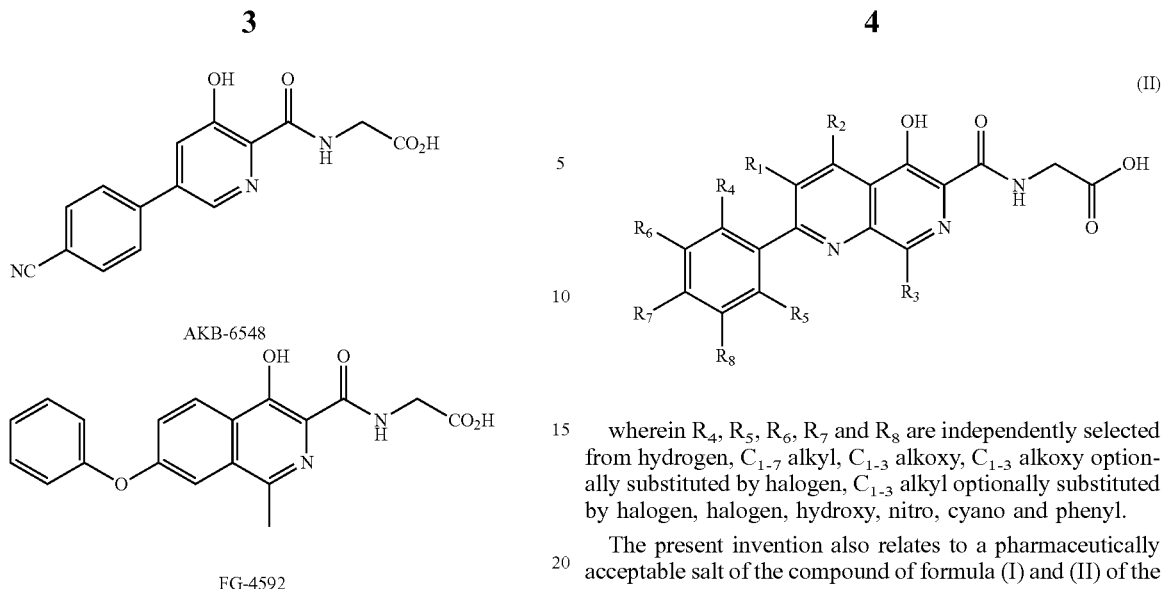

wherein $R_4$, $R_5$, $R_6$, $R_7$ and $R_8$ are independently selected from hydrogen, $C_{1-7}$ alkyl, $C_{1-3}$ alkoxy, $C_{1-3}$ alkoxy optionally substituted by halogen, $C_{1-3}$ alkyl optionally substituted by halogen, halogen, hydroxy, nitro, cyano and phenyl.

The present invention also relates to a pharmaceutically acceptable salt of the compound of formula (I) and (II) of the present invention, and preferably a pharmaceutically acceptable base addition salt that is formed by reacting the compound of the present invention with a pharmaceutically acceptable base. The pharmaceutically acceptable bases include, but are not limited to, sodium hydroxide, sodium carbonate, potassium hydroxide, potassium carbonate, magnesium hydroxide, magnesium oxide, calcium hydroxide, calcium oxide, diethanolamine, lysine, ethanolamine, diethylamine, piperazine and the like.

The most preferred compounds of the present invention are shown in the following table:

| No. | Structure |
|---|---|
| 1 | 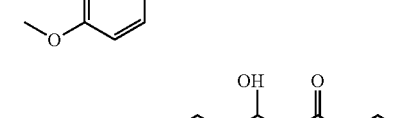 |
| 2 | 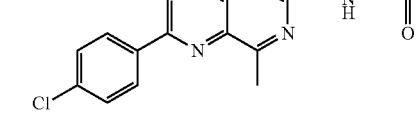 |
| 3 | 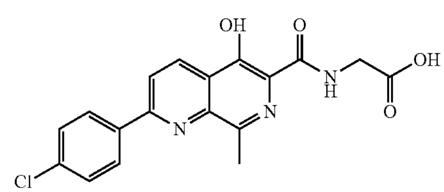 [SMILES: Cc1nc(C(=O)NCC(=O)O)c(O)c2ccc(-c3ccc(Cl)cc3)nc12] |
| 4 | 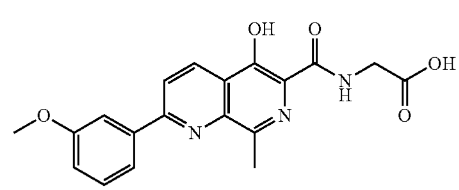 [SMILES: COc1cccc(-c2ccc3c(O)c(C(=O)NCC(=O)O)nc(C)c3n2)c1] |

| No. | Structure |
|---|---|
| 5 | 2-(pyridin-3-yl)-8-methyl-4-hydroxy-1,7-naphthyridine-6-carboxamide-N-glycine |
| 6 | 2-(3-chlorophenyl)-4-hydroxy-1,7-naphthyridine-6-carboxamide-N-glycine |
| 7 | 2-(3-chlorophenyl)-8-methyl-4-hydroxy-1,7-naphthyridine-6-carboxamide-N-glycine |
| 8 | 2-(4-chlorophenyl)-4-hydroxy-1,7-naphthyridine-6-carboxamide-N-glycine |
| 9 | 2-phenyl-8-methyl-4-hydroxy-1,7-naphthyridine-6-carboxamide-N-glycine |
| 10 | 2-(4-methoxyphenyl)-8-methyl-4-hydroxy-1,7-naphthyridine-6-carboxamide-N-glycine |
| 11 | 2-(4-tert-butylphenyl)-8-methyl-4-hydroxy-1,7-naphthyridine-6-carboxamide-N-glycine |
| 12 | 2-(3-bromophenyl)-8-methyl-4-hydroxy-1,7-naphthyridine-6-carboxamide-N-glycine |

| No. | Structure |
|---|---|
| 13 | 2-(3-bromophenyl)-4-hydroxy-1,7-naphthyridine-6-carboxamide-N-glycine |
| 14 | 2-(naphthalen-1-yl)-4-hydroxy-1,7-naphthyridine-6-carboxamide-N-glycine |
| 15 | 2-(3-methoxyphenyl)-4-hydroxy-1,7-naphthyridine-6-carboxamide-N-glycine |
| 16 | 2-(4-tert-butylphenyl)-4-hydroxy-1,7-naphthyridine-6-carboxamide-N-glycine |
| 17 | 2-(4-bromophenyl)-4-hydroxy-1,7-naphthyridine-6-carboxamide-N-glycine |
| 18 | 2-(thiophen-2-yl)-4-hydroxy-1,7-naphthyridine-6-carboxamide-N-glycine |
| 19 | 2-(naphthalen-2-yl)-4-hydroxy-1,7-naphthyridine-6-carboxamide-N-glycine |

| No. | Structure |
|---|---|
| 20 | 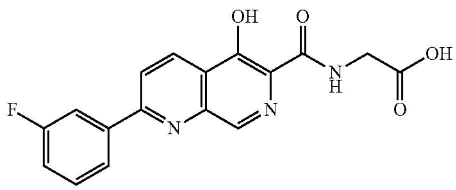 [SMILES: O=C(O)CNC(=O)c1ncc2nc(-c3cccc(F)c3)ccc2c1O] |
| 21 | 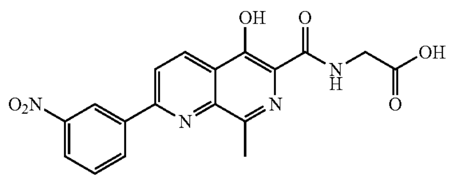 [SMILES: Cc1nc(C(=O)NCC(=O)O)c(O)c2ccc(-c3cccc([N+](=O)[O-])c3)nc12] |
| 22 | 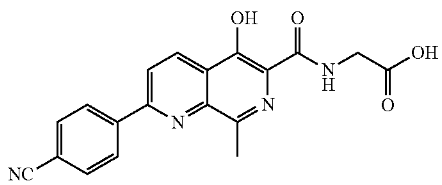 [SMILES: Cc1nc(C(=O)NCC(=O)O)c(O)c2ccc(-c3ccc(C#N)cc3)nc12] |
| 23 | |
| 24 | |
The 5-hydroxy-1,7-naphthyridine compound represented by the structural formulas I and II can be synthesized according to the example as shown in synthesis scheme 1.
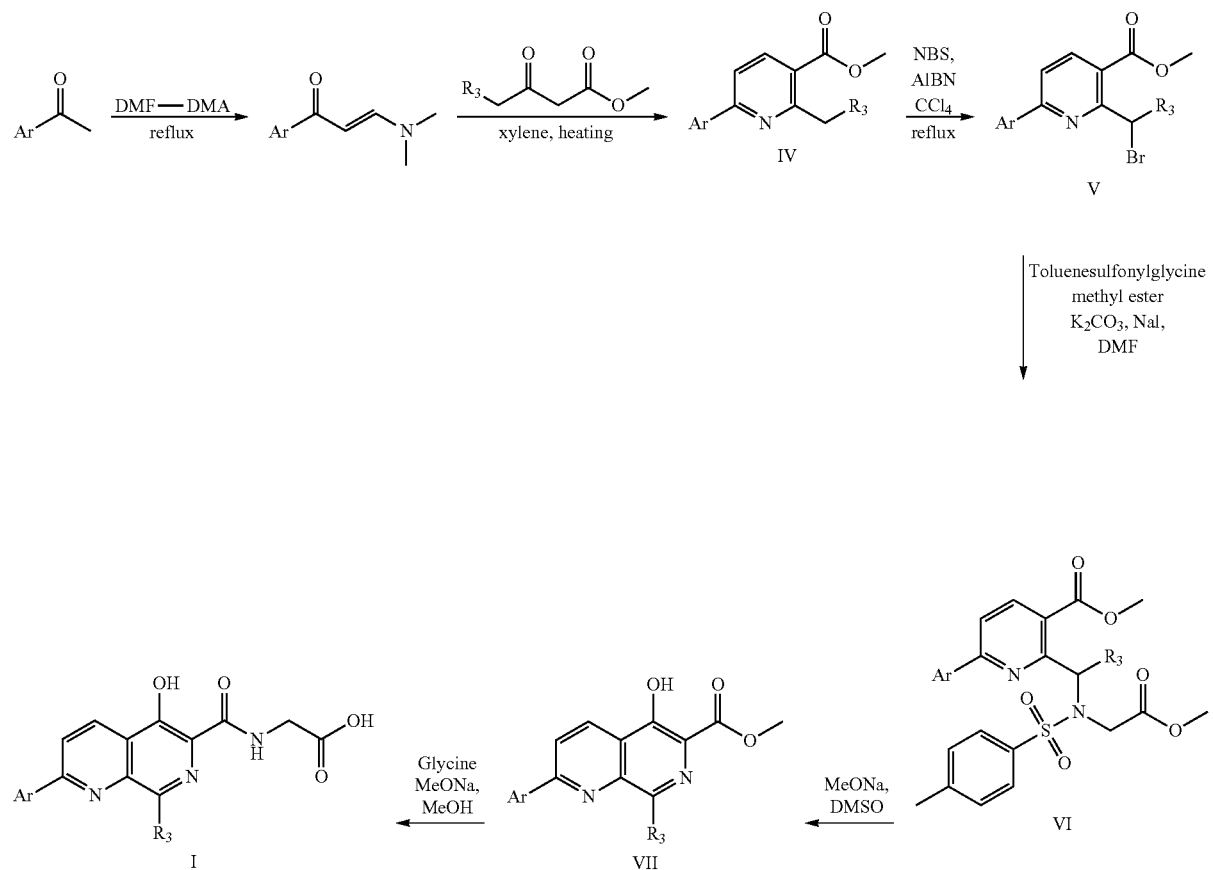
Synthesis scheme 1

In particular, the present invention relates to a method for preparing a compound of claim 1, comprising:

step 1: subjecting the compound of the following formula

and N,N-dimethylformamide dimethylacetal under reflux to condensation reaction, to form a compound of formula (III)

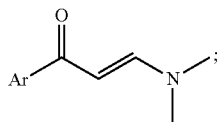

step 2: subjecting the intermediate (III) obtained in step 1 and an $R_3$-substituted methyl acylacetate having the following formula

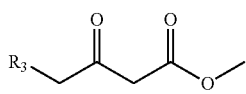

to condensation reaction, to form an intermediate (IV)

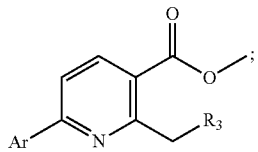

step 3: subjecting the methyl or methylene group in the intermediate (IV) obtained in the step 2 to bromination reaction, to form a bromide intermediate (V)

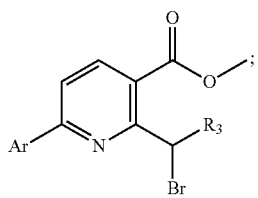

step 4: replacing the intermediate (V) obtained in the step 3 with toluenesulfonylglycine methyl ester to obtain a p-toluenesulfonyl intermediate (VI)

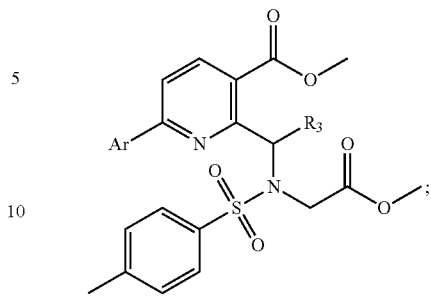

step 5: subjecting the intermediate (VI) obtained in the step 4 to deprotonation at methylene group under basic conditions to form a carbon anion, followed by intramolecular attack on the carbomethoxy on pyridine ring by the carbon anion to form a ketone, and rapidly removing the p-toluenesulfonyl group under basic conditions to form a methyl 5-hydroxy-1,7-naphthyridine formate intermediate (VII)

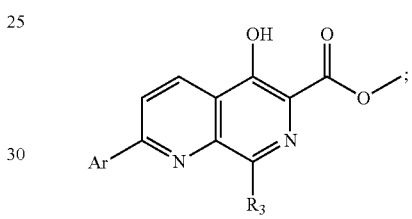

step 6: subjecting the methyl formate of intermediate (VII) obtained in the step 5 and glycine to exchange reaction, to form the compound of formula (I).

Take the compound 2-[5-hydroxy-[2-(4-chloro)-phenyl]-1,7-naphthyridine-6-formamido} acetic acid as an example, the above step 1 comprises subjecting a substituted p-chloroacetophenone and N,N-dimethylformamide dimethylacetal to condensation reaction under heating conditions to remove two molecules of methanol, to form 3-dimethylamino-1-(4-methoxy-phenyl)-propenone (Ill). Preferred solvents include toluene, xylene, and the reaction is carried out under reflux conditions.

The above step 2 comprises subjecting (3-dimethylamino-1-(4-methoxy-phenyl)-propenone (III) and methyl acetoacetate in the presence of ammonium salt and catalyst under heating conditions to condensation reaction, to form methyl 6-(4-chloro-phenyl)-2-methyl-nicotinate (IV). Preferred ammonium salts include ammonium carbonate, ammonium bicarbonate, ammonium chloride, ammonium acetate and the like. Preferred catalysts include Lewis acids such as cerium$^{(III)}$ chloride, Sn$^{(IV)}$Cl$_4$, Ti$^{(IV)}$Cl$_4$, Zn$^{(II)}$Cl$_2$, Al$^{(III)}$Cl$_3$, boron trifluoride etherate. Preferred Lewis acid enhancer is sodium iodide. Preferred reaction solvents include ethanol, methanol, isopropanol, t-butanol and the like. The reaction is carried out under reflux.

The above step 3 comprises subjecting the methyl at the 2-position of the pyridine ring of methyl 6-(4-chloro-phenyl)-2-methyl-nicotinate (IV) to a free radical bromination reaction. Preferred brominating reagents include N-bromosuccinimide, dibromohydantoin, cuprous$^{(II)}$ bromide, liquid bromine and the like. Preferred bromination reaction initiators include azobisisobutyronitrile (AIBN), benzoyl peroxide and the like. Preferred bromination reaction solvents include carbon tetrachloride, dichloromethane and chloroform. The reaction is carried out under reflux, to obtain a bromide intermediate methyl 2-bromomethyl-6-(4-chloro-phenyl)-nicotinate (V).

The above step 4 comprises reacting methyl 2-bromomethyl-6-(4-chloro-phenyl)-nicotinate (V) with p-toluenesulfonylglycine methyl ester under the catalysis of the base, to form methyl 6-(4-chloro-phenyl)-2-{[methoxycarbonylmethyl-(4-methylphenylsulfonyl)-amino]-methyl}-nicotinate (VI). Preferred bases include potassium carbonate, cesium carbonate, sodium carbonate. Preferred reaction solvents include N,N-dimethylformamide, N-methylpyrrolidone, N,N-dimethylacetamide, dimethylsulfoxide and the like. Preferred reaction temperature is 20~80° C.

The above step 5 comprises subjecting methyl 6-(4-chloro-phenyl)-2-{[methoxycarbonylmethyl-(4-methylphenyl sulfonyl)-amino]-methyl}-nicotinate (VI) to intramolecular cyclization under basis conditions, meanwhile removing the p-toluenesulfonyl group, to form methyl 2-(4-chloro-phenyl)-5-hydroxy-[1,7] naphthyridine-6-carboxylate (VII). Preferred bases include sodium methoxide, sodium ethoxide, potassium tert-butoxide, sodium tert-butoxide. Preferred reaction solvents include N,N-dimethylformamide, N-methylpyrrolidone, N,N-dimethylacetamide, dimethyl sulfoxide, methanol, ethanol, tetrahydrofuran and the like. Preferred reaction temperature is 0~40° C.; and preferred reaction time is 0.5~3 hours.

The above step 6 comprises subjecting methyl 2-(4-chloro-phenyl)-5-hydroxy-[1,7]-naphthyridine-6-carboxylate (VII) and glycine to replacement reaction under basic conditions in a confined heating environment to directly replace methyl carboxylate group in methyl 2-(4-chloro-phenyl)-5-hydroxy-[1,7]-naphthyridine-6-carboxylate into formamido acetic acid, to form 2-{5-hydroxy-[2-(4-chloro)-phenyl]-1,7-naphthyridine-6-formamido} acetic acid, the target product of Example 1. Preferred bases include sodium methoxide, sodium ethoxide, potassium tert-butoxide, sodium tert-butoxide and the like. Preferred reaction solvents include methanol, ethanol, isopropanol, and n-butanol. Preferred reaction temperature is 80~140° C.

Further the present invention provides a pharmaceutical composition comprising a 5-hydroxy-1,7-naphthyridine compound corresponding to formula (I) for inhibition of HIF prolyl hydroxylase and generation of endogenous EPO. The composition of the present invention comprises at least one 5-hydroxy-1,7-naphthyridine compound of formula (I) or a salt thereof.

The present invention also relates to a use of the compound of the invention or a pharmaceutically acceptable salt thereof in the preparation of a medicament for inhibiting HIF prolyl hydroxylase; a use of the compound of the invention in the preparation of a medicament for promoting the generation of endogenous EPO; a use of the compound of the invention in the preparation of a medicament for stabilizing hypoxia-inducible factor α; a use of the compound of the invention in the preparation of a medicament for treating chronic disease-related anemia in a subject, wherein the chronic disease-related anemia is selected from the group consisting of rheumatoid arthritis, rheumatic fever and inflammatory bowel disease; a use of the compound of the invention in the preparation of a medicament for increasing the production of inflammatory cytokines in a subject, wherein the inflammatory cytokines include tumor necrosis factor, interleukin and interferon; a use of the compound of the invention in the preparation of a medicament for treating anemia in a subject that is resistant to the treatment of exogenous erythropoietin administration, wherein the compound enhances the response of hematopoietic precursor cells to the erythropoietin; a use of the compound of the invention in the preparation of a medicament for increasing the production of a factor required for iron ingestion, iron transport and iron utilization in a subject, wherein the factor is selected from the group consisting of erythrocyte aminolevulinic acid synthase, transferrin, transferrin receptor and plasma ceruloplasmin.

The present invention also relates to a method for inhibiting HIF prolyl hydroxylase in a subject comprising administering to the subject a compound of the invention or a pharmaceutically acceptable salt thereof; to a method for promoting the generation of endogenous EPO in a subject comprising administering to the subject a compound of the invention or a pharmaceutically acceptable salt thereof; to a method for stabilizing hypoxia-inducible factor α in a subject comprising administering to the subject a compound of the invention or a pharmaceutically acceptable salt thereof; to a method for treating chronic disease-related anemia in a subject comprising administering to the subject a compound of the invention or a pharmaceutically acceptable salt thereof, wherein the chronic disease-related anemia is selected from the group consisting of rheumatoid arthritis, rheumatic fever and inflammatory bowel disease.

The present invention also relates to a method for increasing the production of inflammatory cytokines in a subject comprising administering to the subject a compound of the invention or a pharmaceutically acceptable salt thereof, wherein the inflammatory cytokines include tumor necrosis factor, interleukin and interferon.

A further aspect of the present invention relates to a method for treating anemia in a subject that is resistant to the treatment of exogenous erythropoietin administration comprising administering to the subject a compound of the invention or a pharmaceutically acceptable salt thereof, wherein the compound enhances the response of hematopoietic precursor cells to the erythropoietin.

The present invention also relates to a method for increasing the production of a factor required for iron ingestion, iron transport and iron utilization in a subject comprising administering to the subject a compound of the invention or a pharmaceutically acceptable salt thereof, wherein the factor is selected from the group consisting of erythrocyte aminolevulinic acid synthase, transferrin, transferrin receptor and plasma ceruloplasmin.

DETAILED DESCRIPTION

The following examples of the present invention are for illustrative purposes only and are not intended to limit the invention, and suitable variations of the invention may be made without departing from the spirit and the scope of the invention.

Example 1

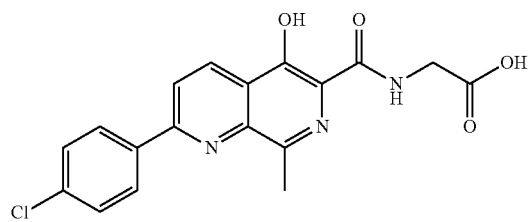 [SMILES: Cc1nc(C(=O)NCC(=O)O)c(O)c2ccc(-c3ccc(Cl)cc3)nc12]

2-{5-hydroxy-[2-(4-chloro)-phenyl]-8-methyl-[1,7]-naphthyridine-6-formamido} acetic acid (Compound No. 3)

Step 1: Preparation of 3-dimethylamino-1-(4-methoxy-phenyl)-propenone 10 g of 4-chloroacetophenone (64.7 mmol, 1.0 equiv.), N,N-dimethyl formamide dimethylacetal (23.1 g, 194.1 mmol, 3.0 equiv.), 50 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 7.5 g of 3-dimethylamino-1-(4-methoxy-phenyl) propenone as a yellow solid, 55.5%.

Step 2: Preparation of methyl 6-(4-chloro-phenyl)-2-ethyl-nicotinate 3.85 g of 3-dimethylamino-1-(4-methoxy-phenyl)-propenone (20.0 mmol, 1.0 equiv.), 2.79 g of methyl propionylacetate (24.0 mmol, 1.2 equiv.), 3.08 g of ammonium acetate (40.0 mmol, 2.0 equiv.), 1.5 g of cerium$^{(III)}$ chloride heptahydrate (4.0 mmol, 0.2 equiv.), 600 mg of sodium iodide (4.0 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.8 g of methyl 6-(4-chloro-phenyl)-2-ethyl-nicotinate as a pale yellow crystal, 58.3%.

Step 3: Preparation of methyl 2-(1-bromoethyl)-6-(4-chloro-phenyl)-nicotinate 3.2 g of methyl 6-(4-chloro-phenyl)-2-ethyl-nicotinate (12.2 mmol, 1.0 equiv.), 2.3 mg of N-bromosuccinimide (12.8 mmol, 1.05 equiv.), 200.1 mg of azobisisobutyronitrile (1.22 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 2.5 g of methyl 2-(1-bromoethyl)-6-(4-chlorophenyl)-nicotinate as a white solid, 60.2%.

Step 4: Preparation of methyl 6-(4-chloro-phenyl)-2-{1-[methoxycarbonyl methyl-(4-methylphenylsulfonyl)-amino]-ethyl}-nicotinate 1.5 g of methyl 2-(l-bromoethyl)-6-(4-chloro-phenyl)-nicotinate (4.4 mmol, 1.0 equiv.), 1.0 g of N-p-toluenesulfonylglycine methyl ester (4.18 mmol, 0.95 equiv.), 1.22 g of potassium carbonate (8.81 mmol, 2.0 equiv.), 67 mg of sodium iodide (0.44 mmol, 0.1 equiv.), 8 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.5 g of methyl 6-(4-chloro-phenyl)-2-{1-[methoxycarbonylmethyl-(4-methylphenylsulfonyl)-amino]-ethyl}-nicotinate as a white solid, 67.6%.

Step 5: Preparation of methyl 2-(4-chloro-phenyl)-5-hydroxy-8-methyl-[1,7]naphthyridine-6-carboxylate At room temperature, a solution of 1 ml of 30% sodium methoxide in methanol was added dropwise to a solution of 1.5 g of methyl 6-(4-chloro-phenyl)-2-{1-[methoxycarbonylmethyl-(4-methylphenylsulfonyl)-amino]-ethyl }-nicotinate (3.0 mmol, 1.0 equiv.) in 10 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 600 mg of methyl 2-(4-chloro-phenyl)-5-hydroxy-8-methyl-[1,7] naphthyridine-6-carboxylate as a yellow solid, 63.7%.

Step 6: Preparation of 2-{5-hydroxy-[2-(4-chloro)-phenyl]-8-methyl-[1,7]-naphthyridine-6-formamido} acetic acid 150 mg of methyl 2-(4-chloro-phenyl)-5-hydroxy-8-methyl-[1,7]naphthyridine-6-carboxylate (0.48 mmol, 1.0 equiv.), 108 mg of glycine (1.44 mmol, 3.0 equiv.), a solution of 250 µl of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 120 mg of 2-{5-hydroxy-[2-(4-chloro)-phenyl]-8-methyl-[1,7]-naphthyridine-6-formamido} acetic acid as an off-white solid, 69.8%.

$^1$H NMR (400 MHz, DMSO-d6) δ 13.65 (s, 1H), 12.83 (s, 1H), 9.43 (t, J=6.2 Hz, 1H), 8.72 (d, J=8.8 Hz, 1H), 8.47 (d, J=8.8 Hz, 1H), 8.36 (d, J=8.2 Hz, 2H), 7.66 (d, J=8.2 Hz, 2H), 4.06 (d, J=6.0 Hz, 2H), 2.92 (s, 3H).

Example 2

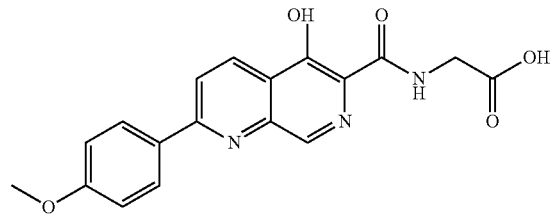 [SMILES: COc1ccc(-c2ccc3c(O)c(C(=O)NCC(=O)O)ncc3n2)cc1]

2-{5-hydroxy-[2-(4-methoxy)-phenyl]-[1,7]-naphthyridine-6-formamido} acetic acid (Compound No. 2)

Step 1: Preparation of 3-dimethylamino-1-(4-methoxy-phenyl)-propenone 15 g of 4-methoxyacetophenone (99.0 mmol, 1.0 equiv.), 35.4 g of N,N-dimethylformamide dimethylacetal (297 mmol, 3.0 equiv.), 100 mL of xylene were refluxed overnight (21 hours). A little raw material was not reacted and the reaction was stopped. The reaction solution was cooled and concentrated to remove xylene. 150 ml of petroleum ether was added to the residue, and a solid precipitated under stirring, followed by filtration to obtain 16.0 g of 3-dimethylamino-1-(4-methoxy-phenyl)-propenone as a yellow solid, 78.8%.

Step 2: Preparation of methyl 6-(4-methoxy-phenyl)-2-methyl-nicotinate 3.0 g of 3-dimethylamino-1-(4-methoxy-phenyl)-propenone (15.9 mmol, 1.0 equiv.), 2.2 g of methyl acetoacetate (19.0 mmol, 1.2 equiv.), 2.45 g of ammonium acetate (31.8 mmol, 2.0 equiv.), 1.2 g of cerium$^{(III)}$ chloride heptahydrate (3.2 mmol, 0.2 equiv.), 480 mg of sodium iodide (3.2 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.0 g of methyl 6-(4-methoxy-phenyl)-2-methyl-nicotinate as a white solid, 53.1%.

Step 3: Preparation of methyl 2-bromomethyl-6-(4-methoxy-phenyl)-nicotinate 1.3 g of methyl 6-(4-methoxy-phenyl)-2-methyl-nicotinate (4.78 mmol, 1.0 equiv.), 894 mg of N-bromosuccinimide (5.02 mmol, 1.05 equiv.), 78.6 mg of azobisisobutyronitrile (0.48 mmol, 0.1 equiv.) and 10 ml of carbon tetrachloride were mixed and refluxed under stirring for 6 hours. The reaction solution was directly subjected to column chromatography, eluting with ethyl acetate/petroleum ether (1:50) to obtain 1.14 g of methyl 2-bromomethyl-6-(4-methoxy-phenyl)-nicotinate as a yellow solid, 67.4%.

Step 4: Preparation of methyl 2-{[methoxycarbonylmethyl-(4-methylphenyl sulfonyl)-amino]-methyl}-6-(4-methoxy-phenyl)-nicotinate 1.1 g of methyl 2-bromomethyl-6-(4-methoxy-phenyl)-nicotinate (3.27 mmol, 1.0 equiv.), 753 mg of N-p-toluenesulfonylglycine methyl ester (3.11 mmol, 0.95 equiv.), 902.5 mg of potassium carbonate (6.54 mmol, 2.0 equiv.), 49.5 mg of sodium iodide (0.33 mmol, 0.1 equiv.), 8 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 500 mg of methyl 2-{[methoxycarbonylmethyl-(4-methylphenylsulfonyl)-amino]-methyl}-6-(4-methoxy-phenyl)-nicotinate as a yellow oil, 31.6%.

Step 5: Preparation of methyl 5-hydroxy-2-(4-methoxy-phenyl)-[1,7]naphthyridine-6-carboxylate At room temperature, a solution of 200 µl of 30% sodium methoxide in methanol was added dropwise to a solution of 500 mg (1.02 mmol, 1.0 equiv.) of methyl 2-{[methoxycarbonylmethyl-(4-methylphenylsulfonyl)-amino]-methyl}-6-(4-methoxy-phenyl)-nicotinate in 7 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 200 mg of methyl 5-hydroxy-2-(4-methoxy-phenyl)-[1,7]naphthyridine-6-carboxylate as a yellow solid, 63.2%.

Step 6: Preparation of 2-{5-hydroxy-[2-(4-methoxy)-phenyl]-[1, 7]-naphthyridine-6-formamido} acetic acid 130 mg of methyl 5-hydroxy-2-(4-methoxy-phenyl)-[1, 7] naphthyridine-6-carboxylate (0.42 mmol, 1.0 equiv.), 95 mg of glycine (1.26 mmol, 3.0 equiv.), a solution of 250 µl of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 70 mg of 2-{5-hydroxy-[2-(4-methoxy)-phenyl]-[1,7]-naphthyridine-6-formamido} acetic acid as an off-white solid, 47.1%.

$^1$H NMR (400 MHz, DMSO-d6) δ 13.59 (s, 1H), 9.41 (br s, 1H), 8.92 (s, 1H), 8.66 (d, J=8.8 Hz, 1H), 8.42 (d, J=8.8 Hz, 1H), 8.37-8.28 (m, 2H), 7.19-7.10 (m, 2H), 4.05 (d, J=6.0 Hz, 2H), 3.88 (s, 3H).

Example 3

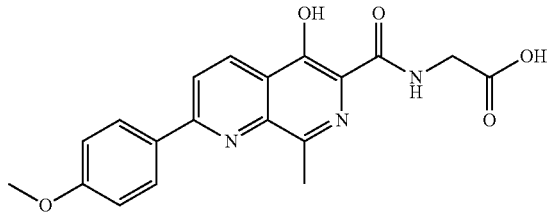 [SMILES: COc1ccc(-c2ccc3c(O)c(C(=O)NCC(=O)O)nc(C)c3n2)cc1]

2-{5-hydroxy-8-methyl-[2-(4-methoxy)-phenyl]-[1, 7]-naphthyridine-6-formamido} acetic acid (Compound No. 10)

Step 1: Preparation of 3-dimethylamino-1-(4-methoxy-phenyl)-propenone 15 g of 4-methoxyacetophenone (99.0 mmol, 1.0 equiv.), N,N-dimethyl formamide dimethylacetal (35.4 g, 297 mmol, 3.0 equiv.), 100 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 16.0 g of 3-dimethylamino-1-(4-methoxy-phenyl)-propenone as a yellow solid, 78.8%.

Step 2: Preparation of methyl 2-ethyl-6-(4-methoxy-phenyl)-nicotinate 3.78 g of 3-dimethylamino-1-(4-methoxy-phenyl)-propenone (20.0 mmol, 1.0 equiv.), 3.12 g of methyl propionylacetate (24.0 mmol, 1.2 equiv.), 3.08 g of ammonium acetate (40.0 mmol, 2.0 equiv.), 900 mg of cerium$^{(III)}$ chloride heptahydrate (2.4 mmol, 0.2 equiv.), 360 mg of sodium iodide (2.4 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 3.0 g of methyl 2-ethyl-6-(4-methoxy-phenyl)-nicotinate as a white solid, 55.4%.

Step 3: Preparation of methyl 2-(1-bromo-ethyl)-6-(4-methoxy-phenyl)-nicotinate 500 mg of methyl 2-ethyl-6-(4-methoxy-phenyl)-nicotinate (1.85 mmol, 1.0 equiv.), 345 mg of N-bromosuccinimide (1.94 mmol, 1.05 equiv.), 30.4 mg of azobisisobutyronitrile (0.18 mmol, 0.1 equiv.) and 10 ml of carbon tetrachloride were mixed and refluxed under stirring for 6 hours. The reaction solution was directly subjected to column chromatography, eluting with ethyl acetate/petroleum ether (1:50) to obtain 470 mg of methyl 2-(1-bromo-ethyl)-6-(4-methoxy-phenyl)-nicotinate as a white solid, 72.7%.

Step 4: Preparation of methyl 2-{1-[methoxycarbonylmethyl-(4-methyl phenylsulfonyl)-amino]-ethyl}-6-(4-methoxy-phenyl)-nicotinate 470 mg of methyl 2-(1-bromo-ethyl)-6-(4-methoxy-phenyl)-nicotinate (1.34 mmol, 1.0 equiv.), 308 mg of N-p-toluenesulfonylglycine methyl ester (1.27 mmol, 0.95 equiv.), 370 mg of potassium carbonate (2.68 mmol, 2.0 equiv.), 20 mg of sodium iodide (0.13 mmol, 0.1 equiv.), 8 ml of N,N-dimethylformamide were mixed and reacted at 50° C. for 8 hours. The reaction solution was diluted with 10 ml of water, and extracted with 60 ml of ethyl acetate in three parts. The organic layer was concentrated to obtain a residue, which was subjected to column chromatography, eluting with ethyl acetate/petroleum ether (1:10-1:1) to obtain 350 mg of methyl 2-{1-[methoxycarbonylmethyl-(4-methylphenylsulfonyl)-amino]-ethyl}-6-(4-methoxy-phenyl)-nicotinate as a pale yellow oil, 51%.

Step 5: Preparation of methyl 5-hydroxy-2-(4-methoxy-phenyl)-8-methyl-[1,7]naphthyridine-6-carboxylate At room temperature, a solution of 300 µl of 30% sodium methoxide in methanol was added dropwise to a solution of 350 mg of methyl 2-{1-[methoxycarbonyl methyl-(4-methylphenylsulfonyl)-amino]-ethyl}-6-(4-methoxy-phenyl)-nicotinate (0.68 mmol, 1.0 equiv.) in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 170 mg of methyl 5-hydroxy-2-(4-methoxy-phenyl)-8-methyl-[1,7] naphthyridine-6-carboxylate as a white solid, 76.9%.

Step 6: Preparation of 2-{5-hydroxy-8-methyl-[2-(4-methoxy)-phenyl]-[1,7]-naphthyridine-6-formamido} acetic acid 170 mg of methyl 5-hydroxy-2-(4-methoxy-phenyl)-8-methyl-[1,7]naphthyridine-6-carboxylate (0.52 mmol, 1.0 equiv.), 95 mg of glycine (1.26 mmol, 3.0 equiv.), a solution of 1.0 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 130 mg of 2-{5-hydroxy-8-methyl-[2-(4-methoxy)-phenyl]-[1,7]-naphthyridine-6-formamido} acetic acid as a pale yellow solid, 68.1%.

$^1$H NMR (400 MHz, DMSO-d6) δ 13.30 (s, 1H), 12.85 (s, 1H), 9.19 (t, J=6.2 Hz, 1H), 8.64 (d, J=8.8 Hz, 1H), 8.42 (d, J=8.8 Hz, 1H), 8.39-8.30 (m, 2H), 7.20-7.11 (m, 2H), 4.08 (d, J=6.2 Hz, 2H), 3.88 (s, 3H), 2.96 (s, 3H).

Example 4

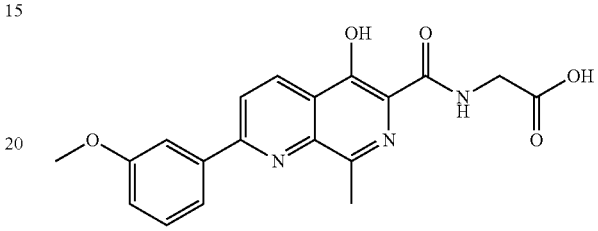

2-{5-hydroxy-[2-(3-methoxy)-phenyl]-8-methyl-[1,7]-napthyridine-6-formamido} acetic acid (Compound No. 4)

Step 1: Preparation of 3-dimethylamino-1-(3-methoxy-phenyl)-propenone 10.0 g of 3-methoxyacetophenone (66.6 mmol, 1.0 equiv.), 23.8 g of N, N-dimethylformamide dimethylacetal (199.8 mmol, 3.0 equiv.), 50 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 10.0 g of 3-dimethylamino-1-(3-methoxy-phenyl)-propenone as a reddish-brown oil, 73.2%.

Step 2: Preparation of methyl 2-ethyl-6-(3-methoxy-phenyl)-nicotinate 3.78 g of 3-dimethylamino-1-(3-methoxy-phenyl)-propenone (20.0 mmol, 1.0 equiv.), 3.12 g of methyl propionylacetate (24.0 mmol, 1.2 equiv.), 3.08 g of ammonium acetate (40.0 mmol, 2.0 equiv.), 1.5 g of cerium$^{(III)}$ chloride heptahydrate (4.0 mmol, 0.2 equiv.), 600 mg of sodium iodide (4.0 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 3 g of methyl 2-ethyl-6-(3-methoxy-phenyl)-nicotinate as a yellow liquid, 55.3%.

Step 3: Preparation of methyl 6-(1-bromoethyl)-2-(3-methoxy-phenyl)-5-carboxylate 2.0 g of methyl 2-ethyl-6-(3-methoxy-phenyl)-nicotinate (8.23 mmol, 1.0 equiv.), 1.54 g of N-bromosuccinimide (8.64 mmol, 1.05 equiv.), 135 mg of azobisisobutyronitrile (0.82 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 1.5 g of methyl 6-(1-bromoethyl)-2-(3-methoxyphenyl)-5-carboxylate as a pale yellow solid, 57.0%.

Step 4: Preparation of methyl 6-{1-[methoxycarbonylmethyl-(4-methyl phenylsulfonyl)-amino]-ethyl}-2-(3-methoxy-phenyl)-5-carboxylate 1.1 g of methyl 6-(1-bromoethyl)-2-(3-methoxy-phenyl)-5-carboxylate (3.43 mmol, 1.0 equiv.), 790 mg of N-p-toluenesulfonylglycine methyl ester (3.26 mmol, 0.95 equiv.), 946.7 mg of potassium carbonate (6.86 mmol, 2.0 equiv.), 51 mg of sodium iodide (0.34 mmol, 0.1 equiv.), 8 ml of N,N-dimethylformamide were mixed and reacted at 50° C. for 8 hours. The reaction solution was diluted with 10 ml of water, and extracted with 60 ml of ethyl acetate in three parts. The organic layer was concentrated to obtain a residue, which was subjected to column chromatography, eluting with ethyl acetate/petroleum ether (1:10-1:1) to obtain 450 mg of methyl 6-{1-[methoxycarbonylmethyl-(4-methylphenylsulfonyl)-amino]-ethyl}-2-(3-methoxy-phenyl)-5-carboxylate as a yellow solid, 27.2%.

Step 5: Preparation of methyl 5-hydroxy-2-(3-methoxy-phenyl)-8-methyl-[1,7]naphthyridine-6-carboxylate At room temperature, a solution of 300 μl of 30% sodium methoxide in methanol was added dropwise to a solution of 450 mg of methyl 6-{1-[methoxycarbonyl methyl-(4-methylphenylsulfonyl)-amino]-ethyl}-2-(3-methoxy-phenyl)-5-carboxylate in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 100 mg of methyl 5-hydroxy-2-(3-methoxy-phenyl)-8-methyl-[1,7]naphthyridine-6-carboxylate as a white solid, 36.4%.

Step 6: Preparation of 2-{5-hydroxy-[2-(3-methoxy)-phenyl]-8-methyl-[1,7]-naphthyridine-6-formamido} acetic acid 100 mg of methyl 5-hydroxy-2-(3-methoxy-phenyl)-8-methyl-[1,7]naphthyridine-6-carboxylate (0.34 mmol, 1.0 equiv.), 76 mg of glycine (1.02 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 70 mg of 2-{5-hydroxy-[2-(3-methoxy)-phenyl]-8-methyl-[1,7]-naphthyridine-6-formamido} acetic acid as a yellow-brown solid, 61.6%.

$^1$H NMR (400 MHz, DMSO-d6) $^1$H NMR (400 MHz, DMSO-d6) δ 13.67 (s, 1H), 12.83 (s, 1H), 9.46 (t, J=6.0 Hz, 1H), 8.70 (d, J=8.8 Hz, 1H), 8.49 (d, J=8.8 Hz, 1H), 7.98-7.89 (m, 2H), 7.53 (t, J=8.0 Hz, 1H), 7.20-7.16 (m, 1H), 4.07 (d, J=6.0 Hz, 2H), 3.90 (s, 3H).

Example 5

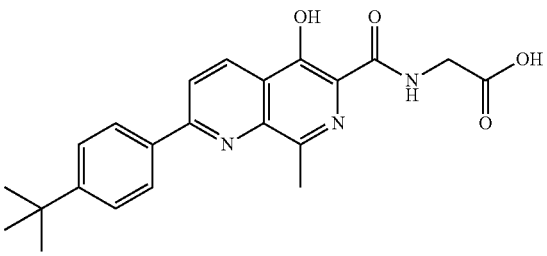 [SMILES: Cc1nc(C(=O)NCC(=O)O)c(O)c2ccc(-c3ccc(C(C)(C)C)cc3)nc12]

2-{5-hydroxy-8-methyl-[2-(4-tert-butyl)-phenyl]-[1,7]-naphthyridine-6-formamido} acetic acid (Compound No. 11)

Step 1: Preparation of 1-(4-tert-butyl-phenyl)-3-dimethylamino-propenone 10 g of 4-tert-butylacetophenone (56.7 mmol, 1.0 equiv.), 20.3 g of N,N-dimethylformamide dimethylacetal (170 mmol, 3.0 equiv.), 50 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 7.0 g of 1-(4-tert-butyl-phenyl)-3-dimethylamino-propenone as a pale yellow solid, 53.4%.

Step 2: Preparation of methyl 6-(4-tert-butyl-phenyl)-2-ethyl-nicotinate 3.0 g of 1-(4-tert-butyl-phenyl)-3-dimethylamino-propenone (12.9 mmol, 1.0 equiv.), 2.0 g of methyl propionylacetate (15.4 mmol, 1.2 equiv.), 2.0 g of ammonium acetate (25.8 mmol, 2.0 equiv.), 483 mg of cerium$^{(III)}$ chloride heptahydrate (1.29 mmol, 0.2 equiv.), 194 mg of sodium iodide (1.29 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.0 g of methyl 6-(4-tert-butyl-phenyl)-2-ethyl-nicotinate as a yellow liquid, 52.2%.

Step 3: Preparation of methyl 2-(1-bromoethyl)-6-(4-tert-butyl-phenyl)-nicotinate 1.8 g of methyl 6-(4-tert-butyl-phenyl)-2-ethyl-nicotinate (6.06 mmol, 1.0 equiv.), 1.13 g of N-bromosuccinimide (6.36 mmol, 1.05 equiv.), 100 mg of azobisisobutyronitrile (0.6 mmol, 0.1 equiv.) and 10 ml of carbon tetrachloride were mixed and refluxed under stirring for 6 hours. The reaction solution was directly subjected to column chromatography, eluting with ethyl acetate/petroleum ether (1:50) to obtain 1.5 g of methyl 2-(1-bromo-ethyl)-6-(4-tert-butyl-phenyl)-nicotinate as a yellow liquid, 66.8%.

Step 4: Preparation of methyl 6-(4-tert-butyl-phenyl)-2-{1-[methoxycarbonyl methyl-(4-methylphenylsulfonyl)-amino]-ethyl}-nicotinate 1.5 g of methyl 2-(l-bromo-ethyl)-6-(4-tert-butyl-phenyl)-nicotinate (4.0 mmol, 1.0 equiv.), 919 mg of N-p-toluene-sulfonylglycine methyl ester (3.78 mmol, 0.95 equiv.), 1.1 g of potassium carbonate (8.0 mmol, 2.0 equiv.), 60 mg of sodium iodide (0.4 mmol, 0.1 equiv.), 10 ml of N,N-dimethylformamide were mixed and reacted at 50° C. for 8 hours. The reaction solution was diluted with 10 ml of water, and extracted with 60 ml of ethyl acetate in three parts. The organic layer was concentrated to obtain a residue, which was subjected to column chromatography, eluting with ethyl acetate/petroleum ether (1:10-1:1) to obtain 600 mg of methyl 6-(4-tert-butyl-phenyl)-2-{1-[methoxycarbonylmethyl-(4-methylphenylsulfonyl)-amino]-ethyl}-nicotinate as a yellow oil, 27.9%.

Step 5: Preparation of methyl 2-(4-tert-butyl-phenyl)-5-hydroxy-8-methyl-[1,7] naphthyridine-6-carboxylate At room temperature, a solution of 300l of 30% sodium methoxide in methanol was added dropwise to a solution of 600 mg of methyl 6-(4-tert-butyl-phenyl)-2-{1-[methoxycarbonylhnethyl-(4-methylphenylsulfonyl)-amino]-ethyl}-nicotinate (0.68 mmol, 1.0 equiv.) in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 200 mg of methyl 2-(4-tert-butyl-phenyl)-5-hydroxy-8-methyl-[1,7] naphthyridine-6-carboxylate as a white solid, 84%.

Step 6: Preparation of 2-{5-hydroxy-8-methyl-[2-(4-tert-butyl)-phenyl]-[1,7]-naphthyridine-6-formamido} acetic acid 200 mg of methyl 2-(4-tert-butyl-phenyl)-5-hydroxy-8-methyl-[1,7]naphthyridine-6-carboxylate (0.57 mmol, 1.0 equiv.), 129 mg of glycine (1.71 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 150 mg of 2-{5-hydroxy-8-methyl-[2-(4-tert-butyl)-phenyl]-[1,7]-naphthyridine-6-formamido} acetic acid as a yellow solid, 66.0%.

$^1$H NMR (400 MHz, DMSO-d6) δ 13.37 (s, 1H), 9.21 (br s, 1H), 8.70 (d, J=8.8 Hz, 1H), 8.44 (d, J=8.8 Hz, 1H), 8.32-8.25 (m, 2H), 7.66-7.59 (m, 2H), 4.06 (d, J=6.4 Hz, 2H), 2.97 (s, 3H), 1.37 (s, 9H).

Example 6

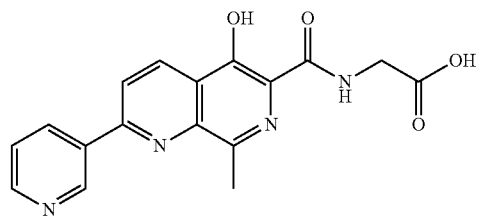 [SMILES: Cc1nc(C(=O)NCC(=O)O)c(O)c2ccc(-c3cccnc3)nc12]

2-{5-hydroxy-8-methyl-[2-(3-pyridyl)]-[1,7]-naphthyridine-6-formamido} acetic acid (Compound No. 5)

Step 1: Preparation of 3-dimethylamino-1-pyridin-3-yl-propenone 10 g of 3-acetylpyridine (82 mmol, 1.0 equiv.), 29.3 g of N, N-dimethylformamide dimethylacetal (246 mmol, 3.0 equiv), and 50 ml of xylene were refluxed overnight (21 hours). A little raw material was not reacted and the reaction was stopped. The reaction solution was cooled and concentrated to remove xylene. 150 ml of petroleum ether was added to the residue, and a solid precipitated under stirring, followed by filtration to obtain 12.0 g of 3-dimethylamino-1-pyridin-3-yl-propenone as a yellow solid, 83.3%.

Step 2: Preparation of methyl 6-ethyl-[2,3']bipyridyl-5-carboxylate 4.83 g of 3-dimethylamino-1-pyridin-3-yl-propenone (30.0 mmol, 1.0 equiv), 4.68 g of methyl propionylacetate (36.0 mmol, 1.2 equiv.), 4.62 g of ammonium acetate (60.0 mmol, 0.2 equiv.), 2.25 g of cerium$^{(III)}$ chloride heptahydrate (6.0 mmol, 0.2 equiv.), 900 mg of sodium iodide (6.0 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 4.5 g of methyl 6-ethyl-[2,3'] bipyridyl-5-carboxylate as a yellow solid, 61.9%.

Step 3: Preparation of methyl 6-(1-bromoethyl)-[2, 3'] bipyridyl-5-carboxylate 3.0 g of methyl 6-ethyl-[2, 3'] bipyridyl-5-carboxylate (11.1 mmol, 1.0 equiv.), 2.07 g of N-bromosuccinimide (11.66 mmol, 1.05 equiv.)), 182 mg of azobisisobutyronitrile (1.12 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 2.5 g of methyl 6-(1-bromoethyl)-[2,3'] bipyridyl-5-carboxylate as a yellow liquid, 64.6%.

Step 4: Preparation of methyl 6-(1-(N-(2-methoxy-2-oxoethyl)-4-methyl benzenesulfonamido) propan-2-yl)-[2, 3'] bipyridyl-5-carboxylate 2.5 g of methyl 6-(1-bromoethyl)-[2, 3'] bipyridyl-5-carboxylate (7.16 mmol, 1.0 equiv.), 1.65 g of N-p-toluene-sulfonylglycine methyl ester (6.8 mmol, 0.95 equiv.), 1.98 g of potassium carbonate (14.3 mmol, 2.0 equiv.), 108 mg of sodium iodide (0.72 mmol, 0.1 eq.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.0 g of methyl 6-(1-(N-(2-methoxy-2-oxoethyl)-4-methylbenzenesulfonamido) propan-2-yl)-[2, 3']bipyridyl-5-carboxylate as a yellow oil, 27.3%.

Step 5: Preparation of methyl 5-hydroxy-8-methyl-2-(3-pyridyl)-[1,7]-naphthyridine-6-carboxylate At room temperature, a solution of 600 μl of 30% sodium methoxide in methanol was added dropwise to a solution of 1.0 g (1.95 mmol, 1.0 equiv.) of methyl 6-(1-(N-(2-methoxy-2-oxoethyl)-4-methylbenzenesulfonamido) propan-2-yl)-[2, 3'] bipyridyl-5-carboxylate in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 200 mg of methyl 5-hydroxy-8-methyl-2-(3-pyridyl)-[1,7]-naphthyridine-6-carboxylate as a pale yellow solid, 31.6%.

Step 6: Preparation of 2-{5-hydroxy-8-methyl-2-pyridine-[1,7]-naphthyridine-6-formamido} acetic acid 200 mg of methyl 5-hydroxy-8-methyl-2-(3-pyridyl)-[1,7]-naphthyridine-6-carboxylate (0.62 mmol, 1.0 equiv.), 140 mg of glycine (1.86 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 130 mg of 2-{5-hydroxy-8-methyl-2-pyridine-[1, 7]-naphthyridine-6-formamido} acetic acid as an off-white solid, 57.0%.

$^1$H NMR (400 MHz, DMSO-d6) δ 13.39 (s, 1H), 12.83 (s, 1H), 9.57-9.52 (m, 1H), 9.25 (br s, 1H), 8.80-8.76 (m, 2H), 8.75-8.70 (m, 1H), 8.58 (d, J=8.8 Hz, 1H), 7.66 (dd, J=8.0, 4.8 Hz, 1H), 4.07 (d, J=6.0 Hz, 2H), 3.00 (s, 3H).

Example 7

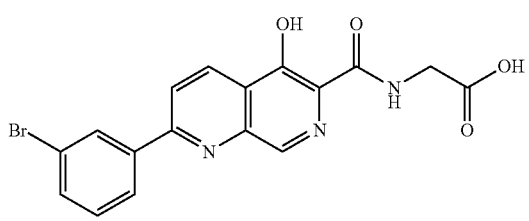 [SMILES: O=C(O)CNC(=O)c1ncc2nc(-c3cccc(Cl)c3)ccc2c1O]

2-{5-hydroxy-2-(3-bromophenyl)-[1,7]-naphthyridine-6-formamido} acetic acid (Compound No. 13)

Step 1: Preparation of 1-(3-bromo-phenyl)-3-dimethylamino-propenone 10.0 g of 3-bromoacetophenone (50.2 mmol, 1.0 equiv.), 18.0 g of N,N-dimethylformamide dimethylacetal (150.7 mmol, 3.0 equiv.), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 7.0 g of 1-(3-bromo-phenyl)-3-dimethylamino-propenone as a yellow solid, 55.1%.

Step 2: Preparation of methyl 6-(3-bromo-phenyl)-2-methyl-nicotinate 2.6 g of 1-(3-bromo-phenyl)-3-dimethylamino-propenone (10.2 mmol, 1.0 equiv.), 1.59 g of methyl acetoacetate (12.2 mmol, 1.2 equiv.), 1.57 g of ammonium acetate (20.4 mmol, 2.0 equiv.), 765 mg of cerium$^{(III)}$ chloride heptahydrate (2.04 mmol, 0.2 equiv.), 306 mg of sodium iodide (2.04 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.2 g of methyl 6-(3-bromo-phenyl)-2-methyl-nicotinate as a yellow liquid, 67.7%.

Step 3: Preparation of methyl 2-bromomethyl-6-(3-bromo-phenyl)-nicotinate 2.0 g of methyl 6-(3-bromo-phenyl)-2-methyl-nicotinate (6.25 mmol, 1.0 equiv.), 1.17 g of N-bromosuccinimide (6.56 mmol, 1.05 equiv.), 103 mg of azobisisobutyronitrile (0.62 mmol, 0.1 equiv.) and 10 ml of carbon tetrachloride were mixed and refluxed under stirring for 6 hours. The reaction solution was directly subjected to column chromatography, eluting with ethyl acetate/petroleum ether (1:50) to obtain 1.8 g of methyl 2-bromomethyl-6-(3-bromo-phenyl)-nicotinate as a yellow liquid, 72.6%.

Step 4: Preparation of methyl 6-(3-bromo-phenyl)-2-{[methoxycarbonyl methyl-(4-methylphenylsulfonyl)-amino]-methyl}-nicotinate 2.0 g of methyl 2-bromomethyl-6-(3-bromo-phenyl)-nicotinate (5.0 mmol, 1.0 equiv.), 1.15 mg of N-p-toluenesulfonylglycine methyl ester (4.75 mmol, 0.95 equiv.), 1.38 g of potassium carbonate (10.0 mmol, 2.0 equiv.), 75 mg of sodium iodide (0.5 mmol, 0.1 equiv.), 10 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.0 g of methyl 6-(3-bromo-phenyl)-2-{[methoxycarbonylmethyl-(4-methylphenylsulfonyl)-amino]-methyl}-nicotinate as a yellow oil, 35.7%.

Step 5: Preparation of methyl 2-(3-bromo-phenyl)-5-hydroxy-[1,7]naphthyridine-6-carboxylate At room temperature, a solution of 600l of 30% sodium methoxide in methanol was added dropwise to a solution of 1.0 g (1.78 mmol, 1.0 equiv.) of methyl 6-(3-bromo-phenyl)-2-{[methoxycarbonylmethyl-(4-methylphenylsulfonyl)-amino]-methyl}-nicotinate in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 200 mg of methyl 2-(3-bromo-phenyl)-5-hydroxy-[1,7]naphthyridine-6-carboxylate as a pale yellow solid, 30.2%.

Step 6: Preparation of 2-{5-hydroxy-2-(3-bromophenyl)-[1,7]-naphthyridine-6-formamido} acetic acid 200 mg of methyl 2-(3-bromo-phenyl)-5-hydroxy-[1,7]naphthyridine-6-carboxylate (0.54 mmol, 1.0 equiv.), 121.5 mg of glycine (1.62 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 140 mg of 2-{5-hydroxy-2-(3-bromophenyl)-[1,7]-naphthyridine-6-formamido} acetic acid as a yellow-brown solid, 82.4%.

$^1$H NMR (400 MHz, DMSO-d6) δ 13.42 (s, 1H), 9.46 (t, J=6.0 Hz, 1H), 8.74 (d, J=8.8 Hz, 1H), 8.56-8.49 (m, 2H), 8.36-8.30 (m, 1H), 7.81-7.75 (m, 1H), 7.60-7.53 (t, J=8.0 Hz, 1H), 4.05 (d, J=6.0 Hz, 2H).

Example 8

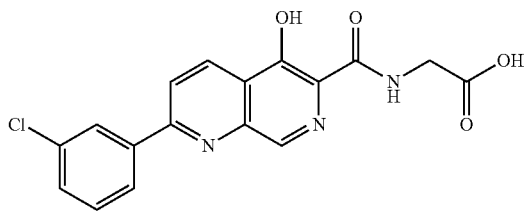

2-{5-hydroxy-[2-(3-chloro)-phenyl]-[1,7]-naphthyridine-6-formamido} acetic acid (Compound No. 6)

Step 1: Preparation of 1-(3-chloro-phenyl)-3-dimethylamino-propenone 10.0 g of 3-chloroacetophenone (64.7 mmol, 1.0 equiv.), 23.1 g of N,N-dimethylformamide dimethylacetal (194.1 mmol, 3.0 equiv.), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 12 g of 1-(3-chloro-phenyl)-3-dimethylamino-propenone as a yellow solid, 88.7%.

Step 2: Preparation of methyl 6-(3-chloro-phenyl)-2-methyl-nicotinate 4.5 g of 1-(3-chloro-phenyl)-3-dimethylamino-propenone (21.5 mmol, 1.0 equiv.), 3.36 g of methyl acetoacetate (25.8 mmol, 1.2 equiv.), 3.31 g of ammonium acetate (43.0 mmol, 2.0 equiv.), 1.61 g of cerium$^{(III)}$ chloride heptahydrate (4.3 mmol, 0.2 equiv.), 645 mg of sodium iodide (4.3 mmol, 0.2 equiv.) and 40 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.9 g of methyl 6-(3-chloro-phenyl)-2-methyl-nicotinate as a pale yellow solid, 49.1%.

Step 3: Preparation of methyl 2-bromomethyl-6-(3-chloro-phenyl)-nicotinate 2.9 g of methyl 6-(3-chloro-phenyl)-2-methyl-nicotinate (10.7 mmol, 1.0 equiv.), 2.0 g of N-bromosuccinimide (11.24 mmol, 1.05 equiv.), 180.6 mg of azobisisobutyronitrile (1.1 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 2.8 g of methyl 2-bromomethyl-6-(3-choro-phenyl)-nicotinate as a yellow liquid, 74.1%.

Step 4: Preparation of methyl 6-(3-chloro-phenyl)-2-{1-[methoxycarbonyl methyl-(4-methylphenylsulfonyl)-amino]-methyl}-nicotinate 2.8 g of methyl 2-bromomethyl-6-(3-chloro-phenyl)-nicotinate (7.91 mmol, 1.0 equiv.), 1.82 g of N-p-toluenesulfonylglycine methyl ester (7.51 mmol, 0.95 equiv.), 2.18 g of potassium carbonate (15.82 mmol, 2.0 equiv.), 118.5 mg of sodium iodide (0.79 mmol, 0.1 equiv.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.3 g of methyl 6-(3-chloro-phenyl)-2-{1-[methoxycarbonylmethyl-(4-methylphenylsulfonyl)-amino]-methyl}-nicotinate as a yellow oil, 31.9%.

Step 5: Preparation of methyl 2-(3-chloro-phenyl)-5-hydroxy-[1,7]naphthyridine-6-carboxylate At room temperature, a solution of 1 ml of 30% sodium methoxide in methanol was added dropwise to a solution of 1.3 g (2.52 mmol, 1.0 equiv.) of methyl 6-(3-chloro-phenyl)-2-{1-[methoxycarbonylmethyl-(4-methylphenyl sulfonyl)-amino]-methyl}-nicotinate in 6 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 400 mg of methyl 2-(3-chloro-phenyl)-5-hydroxy-[1,7]naphthyridine-6-carboxylate as a white solid, 48.4%.

Step 6: Preparation of 2-{5-hydroxy-2-(3-chloro-phenyl)-[1,7]-naphthyridine-6-formamido} acetic acid 200 mg of methyl 2-(3-chloro-phenyl)-5-hydroxy-[1,7]naphthyridine-6-carboxylate (0.61 mmol, 1.0 equiv.), 137 mg of glycine (1.83 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 130 mg of 2-{5-hydroxy-[2-(3-chloro)-phenyl]-[1,7]-naphthyridine-6-formamido} acetic acid as an off-white solid, 65.0%.

$^1$H NMR (400 MHz, DMSO-d6) δ 13.66 (s, 1H), 9.45 (t, J=6.0 Hz, 1H), 8.99 (s, 1H), 8.72 (d, J=8.8 Hz, 1H), 8.50 (d, J=8.8 Hz, 1H), 8.38 (s, 1H), 8.30-8.28 (m, 1H), 7.65-7.61 (m, 2H), 4.06 (d, J=6.0 Hz, 2H).

Example 9

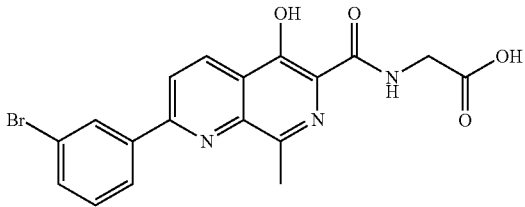 [SMILES: Cc1nc(C(=O)NCC(=O)O)c(O)c2ccc(-c3cccc(Br)c3)nc12]

2-{5-hydroxy-[2-(3-bromo)-phenyl]-8-methyl-[1,7]-naphthyridine-6-formamido} acetic acid (Compound No. 12)

Step 1: Preparation of 1-(3-bromo-phenyl)-3-dimethylamino-propenone 10.0 g of 3-bromoacetophenone (50.2 mmol, 1.0 equiv.), 18.0 g of N,N-dimethylformamide dimethylacetal (150.7 mmol, 3.0 equiv.), 50 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 7.0 g of 1-(3-bromo-phenyl)-3-dimethylamino-propenone as a yellow solid, 55.1%.

Step 2: Preparation of methyl 6-(3-bromo-phenyl)-2-ethyl-nicotinate 4.2 g of 1-(3-bromo-phenyl)-3-dimethylamino-propenone (20.1 mmol, 1.0 equiv.), 2.75 g of methyl propionylacetate (24.1 mmol, 1.2 equiv.), 3.1 g of ammonium acetate (40.2 mmol, 2.0 equiv.), 1.51 g of cerium$^{(III)}$ chloride heptahydrate (4.02 mmol, 0.2 equiv.), 603 mg of sodium iodide (4.02 mmol, 0.2 equiv.) and 40 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 3.7 g of methyl 6-(3-bromo-phenyl)-2-ethyl-nicotinate as a yellow liquid, 60.4%.

Step 3: Preparation of methyl 2-(1-bromoethyl)-6-(3-bromo-phenyl)-nicotinate 4.0 g of methyl 6-(3-bromo-phenyl)-2-ethyl-nicotinate (13.3 mmol, 1.0 equiv.), 2.48 mg of N-bromosuccinimide (14.0 mmol, 1.05 equiv.), 220 mg of azobisisobutyronitrile (1.34 mmol, 0.1 equiv.) and 20 ml of carbon tetrachloride were mixed and refluxed under stirring for 6 hours. The reaction solution was directly subjected to column chromatography, eluting with ethyl acetate/petroleum ether (1:50) to obtain 1.9 g of methyl 2-(1-bromoethyl)-6-(3-bromo-phenyl)-nicotinate as a pale yellow solid, 72.6%.

Step 4: Preparation of methyl 6-(3-bromo-phenyl)-2-{1-[methoxycarbonyl methyl-(4-methylphenylsulfonyl)-amino]-ethyl}-nicotinate 1.9 g of methyl 2-(1-bromoethyl)-6-(3-bromo-phenyl)-nicotinate (5.0 mmol, 1.0 equiv.), 1.15 g of N-p-toluenesulfonylglycine methyl ester (4.75 mmol, 0.95 equiv.), 1.38 g of potassium carbonate (10.0 mmol, 2.0 equiv.), 75 mg of sodium iodide (0.5 mmol, 0.1 equiv.), 10 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 2.5 g of methyl 6-(3-bromo-phenyl)-2-{1-[methoxycarbonylmethyl-(4-methylphenyl sulfonyl)-amino]-ethyl}-nicotinate as a yellow oil, 91.6%.

Step 5: Preparation of methyl 2-(3-bromo-phenyl)-5-hydroxy-8-methyl-[1,7]naphthyridine-6-carboxylate At room temperature, a solution of 3 ml of 30% sodium methoxide in methanol was added dropwise to a solution of 2.5 g of methyl 6-(3-bromo-phenyl)-2-{1-[methoxycarbonylmethyl-(4-m-(4-methylphenyl sulfonyl)-amino]-ethyl}-nicotinate (4.58 mmol, 1.0 equiv.) in 6 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 730 mg of methyl 2-(3-bromo-phenyl)-5-hydroxy-8-methyl-[1,7]naphthyridine-6-carboxylate as a pale yellow solid, 44.5%.

Step 6: Preparation of 2-{5-hydroxy-[2-(3-bromo)-phenyl]-8-methyl-[1,7]-naphthyridine-6-formamido} acetic acid 200 mg of methyl2-(3-chloro-phenyl)-5-hydroxy-8-methyl-[1,7]naphthyridine-6-carboxylate (0.56 mmol, 1.0 equiv.), 129 mg of glycine (1.68 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 170 mg of 2-{5-hydroxy-[2-(3-bromo)-phenyl]-8-methyl-[1,7]-naphthyridine-6-formamido} acetic acid as an yellow-brown solid, 75.7%.

$^1$H NMR (400 MHz, DMSO-d6) δ 13.35 (s, 1H), 12.83 (s, 1H), 9.27-9.20 (m, 1H), 8.72 (d, J=8.8, 1H), 8.55-8.49 (m, 2H), 8.40-8.34 (m, 1H), 7.80-7.78 (m, 1H), 7.58 (t, J=7.2 Hz, 1H), 4.08 (d, J=6.0 Hz, 2H), 2.98 (s, 3H).

Example 10

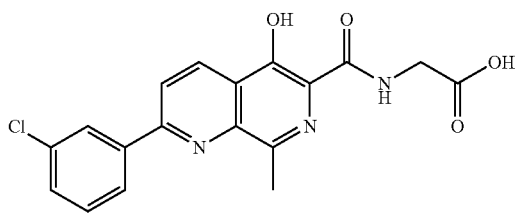 [SMILES: Cc1nc(C(=O)NCC(=O)O)c(O)c2ccc(-c3cccc(Cl)c3)nc12]

2-{5-hydroxy-[2-(3-chloro)-phenyl]-8-methyl-[1,7]-naphthyridine-6-formamido} acetic acid (Compound No. 7)

Step 1: Preparation of 1-(3-chloro-phenyl)-3-dimethylamino-propenone 10.0 g of 3-chloroacetophenone (64.7 mmol, 1.0 equiv.), 23.1 g of N,N-dimethylformamide dimethylacetal (194.1 mmol, 3.0 equiv.), 50 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 12 g of 1-(3-chloro-phenyl)-3-dimethylamino-propenone as a yellow solid, 88.7%.

Step 2: Preparation of methyl 6-(3-chloro-phenyl)-2-ethyl-nicotinate 4.3 g of 1-(3-chloro-phenyl)-3-dimethylamino-propenone (16.9 mmol, 1.0 equiv.), 2.31 g of methyl propionylacetate (20.2 mmol, 1.2 equiv.), 2.6 g of ammonium acetate (33.8 mmol, 2.0 equiv.), 1.27 g of cerium$^{(III)}$ chloride heptahydrate (3.38 mmol, 0.2 equiv.), 507 mg of sodium iodide (3.38 mmol, 0.2 equiv.) and 40 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 3.5 g of methyl 6-(3-chloro-phenyl)-2-ethyl-nicotinate as a pale yellow solid, 79.5%.

Step 3: Preparation of methyl 2-(1-bromoethyl)-6-(3-chloro-phenyl)-nicotinate 3.5 g of methyl 6-(3-chloro-phenyl)-2-ethyl-nicotinate (13.6 mmol, 1.0 equiv.), 2.54 g of N-bromosuccinimide (14.3 mmol, 1.05 equiv.), 223.5 mg of azobisisobutyronitrile (1.36 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 3.4 g of methyl 2-(1-bromoethyl)-6-(3-chloro-phenyl)-nicotinate as a yellow liquid, 85%.

Step 4: Preparation of methyl 6-(3-chloro-phenyl)-2-{1-[methoxycarbonyl methyl-(4-methylphenylsulfonyl)-amino]-ethyl}-nicotinate 3.4 g of methyl 2-(1-bromoethyl)-6-(3-chloro-phenyl)-nicotinate (10.1 mmol, 1.0 equiv.), 2.32 g of N-p-toluene-sulfonylglycine methyl ester (9.6 mmol, 0.95 equiv.), 2.79 g of potassium carbonate (20.2 mmol, 2.0 equiv.), 151.5 mg of sodium iodide (1.01 mmol, 0.1 equiv.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 2.4 g of methyl 6-(3-chloro-phenyl)-2-{1-[methoxycarbonylmethyl-(4-methylphenylsulfonyl)-amino]-ethyl}-nicotinate as a yellow solid, 31.9%.

Step 5: Preparation of methyl 2-(3-chloro-phenyl)-5-hydroxy-8-methyl-[1,7]naphthyridine-6-carboxylate At room temperature, a solution of 4 ml of 30% sodium methoxide in methanol was added dropwise to a solution of 2.4 g of methyl 6-(3-chloro-phenyl)-2-{1-[methoxycarbonylmethyl-(4-methylphenylsulfonyl)-amino]-ethyl}-nicotinate (4.80 mmol, 1.0 equiv.) in 10 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 1.1 g of methyl 2-(3-chloro-phenyl)-5-hydroxy-8-methyl-[1,7]naphthyridine-6-carboxylate as a pale yellow solid, 72.8%.

Step 6: Preparation of 2-{5-hydroxy-[2-(3-chloro)-phenyl]-8-methyl-[1,7]-naphthyridine-6-formamido} acetic acid 200 mg of methyl 2-(3-chloro-phenyl)-5-hydroxy-8-methyl-[1,7]naphthyridine-6-carboxylate (0.64 mmol, 1.0 equiv.), 143 mg of glycine (1.92 mmol, 3.0 equiv.), a solution of 1.0 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 150 mg of 2-{5-hydroxy-[2-(3-chloro)-phenyl]-8-methyl-[1,7]-naphthyridine-6-formamido} acetic acid as a yellow-brown solid, 65.6%.

$^1$H NMR (400 MHz, DMSO-d6) δ 13.29 (s, 1H), 9.16 (br s, 1H), 8.63 (d, J=8.8 Hz, 1H), 8.44 (d, J=8.8 Hz, 1H), 8.33 (s, 1H), 8.31-8.22 (m, 1H), 7.62-7.59 (m, 2H), 4.06 (d, J=6.0 Hz, 2H), 2.92 (s, 3H).

Example 11

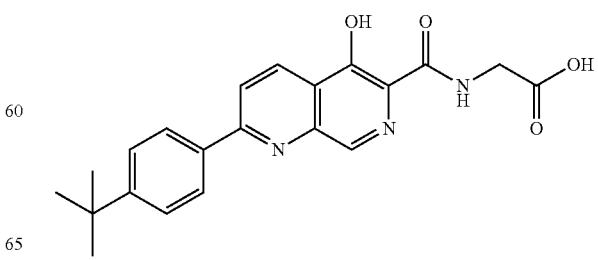

2-{5-hydroxy-[2-(4-tert-butyl)-phenyl]-[1,7]-naphthyridine-6-formamido} acetic acid Step 1: Preparation of 1-(4-tert-butyl-phenyl)-3-dimethylamino-propenone 10 g of 4-tert-butylacetophenone (56.7 mmol, 1.0 equiv.), 20.3 g of N,N-dimethylformamide dimethylacetal (170 mmol, 3.0 equiv.), 50 mL of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 7.0 g of 1-(4-tert-butyl-phenyl)-3-dimethylamino-propenone as a pale yellow solid, 53.4%.

Step 2: Preparation of methyl 6-(4-tert-butyl-phenyl)-2-methyl-nicotinate 5.5 g of 1-(4-tert-butyl-phenyl)-3-dimethylamino-propenone (23.8 mmol, 1.0 equiv.), 3.25 g of methyl acetoacetate (28.6 mmol, 1.2 equiv.), 3.67 g of ammonium acetate (47.6 mmol, 2.0 equiv.), 1.78 g of cerium$^{(III)}$ chloride heptahydrate (4.76 mmol, 0.2 equiv.), 714 mg of sodium iodide (4.76 mmol, 0.2 equiv.) and 50 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 5.4 g of methyl 6-(4-tert-butyl-phenyl)-2-methyl-nicotinate as a yellow liquid, 80.0%.

Step 3: Preparation of methyl 2-bromomethyl-6-(4-tert-butyl-phenyl)-nicotinate 5.4 g of methyl 6-(4-tert-butyl-phenyl)-2-methyl-nicotinate (19.1 mmol, 1.0 equiv.), 3.56 g of N-bromosuccinimide (20.0 mmol, 1.05 equiv.), 312 mg of azobisisobutyronitrile (1.9 mmol, 0.1 equiv.) and 20 ml of carbon tetrachloride were mixed and refluxed under stirring for 6 hours. The reaction solution was directly subjected to column chromatography, eluting with ethyl acetate/petroleum ether (1:50) to obtain 4.0 g of methyl 2-bromomethyl-6-(4-tert-butyl-phenyl)-nicotinate as a yellow oil, 58%.

Step 4: Preparation of methyl 6-(4-tert-butyl-phenyl)-2-{[methoxycarbonyl methyl-(4-methylphenyl-sulfonyl)-amino]-methyl}-nicotinate 4.0 g of methyl 2-bromomethyl-6-(4-tert-butyl-phenyl)-nicotinate (11.1 mmol, 1.0 equiv.), 2.55 g of N-p-toluenesulfonylglycine methyl ester (10.5 mmol, 0.95 equiv.), 3.06 g of potassium carbonate (22.2 mmol, 2.0 equiv.), 166.5 mg of sodium iodide (1.11 mmol, 0.1 equiv.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 4.0 g of methyl 6-(4-tert-butyl-phenyl)-2-{[methoxycarbonylmethyl-(4-methylphenylsulfonyl)-amino]-methyl}-nicotinate as a yellow oil, 68.7%.

Step 5: Preparation of methyl 2-(4-tert-butyl-phenyl)-5-hydroxy-[1,7]naphthyridine-6-carboxylate At room temperature, a solution of 4 ml of 30% sodium methoxide in methanol was added dropwise to a solution of 3.0 g (5.72 mmol, 1.0 equiv.) of methyl 6-(4-tert-butyl-phenyl)-2-{[methoxycarbonylmethyl-(4-methylphenyl sulfonyl)-amino]-methyl}-nicotinate in 10 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 1.4 mg of methyl 2-(4-tert-butyl-phenyl)-5-hydroxy-[1, 7] naphthyridine-6-carboxylate as a yellow solid, 70%.

Step 6: Preparation of 2-{5-hydroxy-[2-(4-tert-butyl)-phenyl]-[1,7]-naphthyridine-6-formamido} acetic acid 250 mg of methyl 2-(4-tert-butyl-phenyl)-5-hydroxy-[1, 7] naphthyridine-6-carboxylate (0.74 mmol, 1.0 equiv.), 167 mg of glycine (2.23 mmol, 3.0 equiv.), a solution of 1.0 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 250 mg of 2-{5-hydroxy-[2-(4-tert-butyl)-phenyl]-[1, 7]-naphthyridine-6-formamido} acetic acid as an off-white solid, 89.1%.

$^1$H NMR (400 MHz, DMSO-d6) δ 13.64 (s, 1H), 12.85 (s, 1H), 9.43 (t, J=6.0 Hz, 1H), 8.96 (s, 1H), 8.70 (d, J=8.8 Hz, 1H), 8.44 (d, J=8.8 Hz, 1H), 8.29-8.22 (m, 2H), 7.65-7.58 (m, 2H), 4.06 (d, J=6.0 Hz, 2H), 1.36 (s, 9H).

Example 12

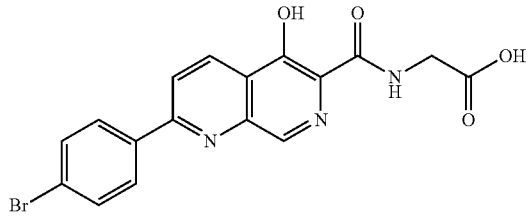 [SMILES: O=C(O)CNC(=O)c1ncc2nc(-c3ccc(Br)cc3)ccc2c1O]

2-{5-hydroxy-[2-(4-bromo)-phenyl]-[1,7]-naphthyridine-6-formamido} acetic acid (Compound No. 17)

Step 1: Preparation of 1-(4-bromo-phenyl)-3-dimethylamino-propenone 10.0 g of 4-bromoacetophenone (50.2 mmol, 1.0 equiv.), 18.0 g of N,N-dimethylformamide dimethylacetal (150.7 mmol, 3.0 equiv.), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 10.4 g of 1-(4-bromo-phenyl)-3-dimethylamino-propenone as a yellow solid, 82.2%.

Step 2: Preparation of methyl 6-(4-bromo-phenyl)-2-methyl-nicotinate 5.0 g of 1-(4-bromo-phenyl)-3-dimethylamino-propenone (19.6 mmol, 1.0 equiv.), 2.68 g of methyl acetoacetate (23.5 mmol, 1.2 equiv.), 3.02 g of ammonium acetate (39.2 mmol, 2.0 equiv.), 881 mg of cerium$^{(III)}$ chloride heptahydrate (2.35 mmol, 0.2 equiv.), 352 mg of sodium iodide (2.35 mmol, 0.2 equiv.) and 40 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 4.7 g of methyl 6-(4-bromo-phenyl)-2-methyl-nicotinate as a yellow solid, 78.33%.

Step 3: Preparation of methyl 2-bromomethyl-6-(4-bromo-phenyl)-nicotinate 4.6 g of methyl 6-(4-bromo-phenyl)-2-methyl-nicotinate (15.3 mmol, 1.0 equiv.), 2.86 g of N-bromosuccinimide (16.06 mmol, 1.05 equiv.), 251.2 mg of azobisisobutyronitrile (1.53 mmol, 0.1 equiv.) and 20 ml of carbon tetrachloride were mixed and refluxed under stirring for 6 hours. The reaction solution was directly subjected to column chromatography, eluting with ethyl acetate/petroleum ether (1:50) to obtain 3.0 g of methyl 2-bromomethyl-6-(4-bromo-phenyl)-nicotinate as a yellow liquid, 51.3%.

Step 4: Preparation of methyl 6-(4-bromo-phenyl)-2-{[methoxycarbonyl methyl-(4-methylphenylsulfonyl)-amino]-methyl}-nicotinate 3.0 g of methyl 2-bromomethyl-6-(4-bromo-phenyl)-nicotinate (7.89 mmol, 1.0 equiv.), 1.81 mg of N-p-toluenesulfonylglycine methyl ester (7.50 mmol, 0.95 equiv.), 2.12 g of potassium carbonate (15.78 mmol, 2.0 equiv.), 118.5 mg of sodium iodide (0.79 mmol, 0.1 equiv.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.1 g of methyl 6-(4-bromo-phenyl)-2-{[methoxycarbonylmethyl-(4-methylphenyl sulfonyl)-amino]-methyl}-nicotinate as a yellow oil, 25.5%.

Step 5: Preparation of methyl 2-(4-bromo-phenyl)-5-hydroxy-[1,7]naphthyridine-6-carboxylate At room temperature, a solution of 1 ml of 30% sodium methoxide in methanol was added dropwise to a solution of 1.1 g (2.0 mmol, 1.0 equiv.) of methyl 6-(4-bromo-phenyl)-2-{[methoxycarbonylmethyl-(4-methylphenyl sulfonyl)-amino]-methyl}-nicotinate in 6 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 150 mg of methyl 2-(4-bromo-phenyl)-5-hydroxy-[1,7] naphthyridine-6-carboxylate as a pale yellow solid, 20.9%.

Step 6: Preparation of 2-{5-hydroxy-[2-(4-bromo)-phenyl]-[1,7]-naphthyridine-6-formamido} acetic acid 120 mg of methyl 2-(4-bromo-phenyl)-5-hydroxy-[1,7] naphthyridine-6-carboxylate (0.34 mmol, 1.0 equiv.), 76.5 mg of glycine (1.02 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 120 mg of 2-{5-hydroxy-[2-(4-bromo)-phenyl]-[1,7]-naphthyridine-6-formamido} acetic acid as a yellow-brown solid, 87.8%.

$^1$H NMR (400 MHz, DMSO-d6) δ13.65 (s, 1H), 12.95 (s, 1H), 9.44 (br s, 1H), 8.96 (s, 1H), 8.72 (d, J=8.8 Hz, 1H), 8.46 (d, J=8.8 Hz, 1H), 8.30-8.22 (m, 2H), 7.95-7.65 (m, 2H), 4.06 (d, J=6.0 Hz, 2H).

Example 13

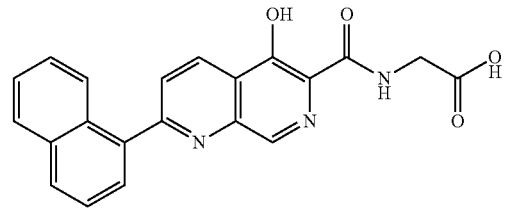 [SMILES: O=C(O)CNC(=O)c1ncc2nc(-c3cccc4ccccc34)ccc2c1O]

[(5-hydroxy-2-(naphthalene-1-yl)-[1,7]naphthyridine-6-carbonyl)-amino]-acetic acid (Compound No. 14)

Step 1: Preparation of 3-dimethylamino-1-(naphthalene-1-yl)-propenone 10.0 g of 1-acetylnaphthalene (58.8 mmol, 1.0 equiv.), 21.0 g of N,N-dimethylformamide dimethylacetal (176.2 mmol, 3.0 equiv), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 10.0 g of 3-dimethylamino-1-naphthalene-1-yl-propenone as a reddish-brown oil, 79.2%.

Step 2: Preparation of methyl 2-methyl-6-(naphthalene-1-yl)-nicotinate 7.5 g of 3-dimethylamino-1-(naphthalene-1-yl)-propenone (33.3 mmol, 1.0 equiv), 4.6 g of methyl acetoacetate (40.0 mmol, 1.2 equiv.), 5.13 g of ammonium acetate (66.6 mmol, 2.0 equiv.), 2.5 g of cerium$^{(III)}$ chloride heptahydrate (6.66 mmol, 0.2 equiv.), 999 mg of sodium iodide (6.66 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 7.0 g of methyl 2-methyl-6-naphthalen-1-yl-nicotinate as a reddish-brown liquid, 75.8%.

Step 3: Preparation of methyl 2-bromomethyl-6-(naphthalen-1-yl)-nicotinate 4.0 g of methyl 2-methyl-6-naphthalen-1-yl-nicotinate (14.4 mmol, 1.0 equiv), 2.69 g of N-bromosuccinimide (15.1 mmol, 1.05 equiv.), 236.2 mg of azobisisobutyronitrile (1.44 mmol, 0.1 equiv.) and 30 ml of carbon tetrachloride were mixed and refluxed under stirring for 6 hours. The reaction solution was directly subjected to column chromatography, eluting with ethyl acetate/petroleum ether (1:50) to obtain 3.0 g of methyl 2-bromomethyl-6-(naphthalen-1-yl)-nicotinate as a yellow liquid, 58.7%

Step 4: Preparation of methyl 2-([methoxycarbonyl-methyl-(4-methylphenyl sulfonyl)-amino]-methyl)-6-(naphthalen-1-yl)-nicotinate 3.0 g of methyl 2-bromomethyl-6-(naphthalen-1-yl)-nicotinate (9.8 mmol, 1.0 equiv), 2.25 g of N-(4-toluenesulfonyl) glycine methyl ester (9.31 mmol, 0.95 equiv.), 2.70 g of potassium carbonate (19.6 mmol, 2.0 equiv.), 147 mg of sodium iodide (0.98 mmol, 0.1 equiv.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.2 g of methyl 2-{[methoxycarbonylmethyl-(4-methylphenylsulfonyl)-amino]-methyl}-6-(naphthalen-1-yl)-nicotinate as a white solid, 23.6%.

Step 5: Preparation of methyl 5-hydroxy-2-(naphthalen-1-yl)-[1,7]naphthyridine-6-carboxylate At room temperature, a solution of 0.6 ml of 30% sodium methoxide in methanol was added dropwise to a solution of 0.6 g (1.16 mmol, 1.0 equiv.) of methyl 2-{[methoxycarbonylmethyl-(4-methylphenylsulfonyl)-amino]-methyl}-6-(naphthalen-1-yl)-nicotinate in 4 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 230 mg of methyl 5-hydroxy-2-(naphthalen-1-yl)-[1,7] naphthyridine-6-carboxylate as a white solid, 60.1%.

Step 6: Preparation of [(5-hydroxy-2-(naphthalen-1-yl)-[1,7] naphthyridine-6-carbonyl)-amino]-acetic acid 150 mg of methyl 5-hydroxy-2-(naphthalen-1-yl)-[1,7] naphthyridine-6-carboxylate (0.45 mmol, 1.0 equiv.), 150 mg of glycine (0.45 mmol, 3.0 equiv.), 1.0 ml solution of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 130 mg of 2[(5-hydroxy-2-(naphthalen-1-yl)-[1,7] naphthyridine-6-carbonyl)-amino]-acetic acid as a white solid, 76.5%.

$^1$H NMR (400 MHz, DMSO-d6) δ 13.74 (s, 1H), 9.56-9.46 (m, 1H), 9.01 (s, 1H), 8.83 (d, J=8.8 Hz, 1H), 8.23-8.15 (m, 2H), 8.14 (d, J=8.0 Hz, 1H), 8.09 (d, J=8.0 Hz, 1H), 7.83 (d, J=6.4 Hz, 1H), 7.72-7.70 (m, 1H), 7.67-7.54 (m, 2H), 4.09 (d, J=6.0 Hz, 2H).

Example 14

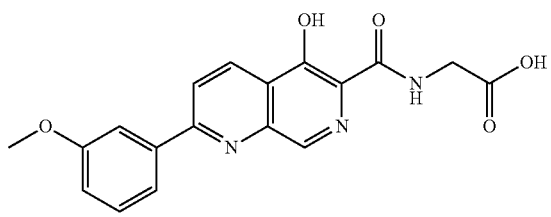 [SMILES: COc1cccc(-c2ccc3c(O)c(C(=O)NCC(=O)O)ncc3n2)c1]

2-{5-hydroxy-[2-(4-methoxy)-phenyl]-[1,7]-naphthyridine-6-formamido} acetic acid (Compound No. 15)

Step 1: Preparation of 3-dimethylamino-1-(3-methoxy-phenyl)-propenone 10.0 g of 3-methoxyacetophenone (66.6 mmol, 1.0 equiv.), 23.8 g of N,N-dimethylformamide dimethylacetal (199.8 mmol, 3.0 equiv.), 50 ml of xylene were refluxed overnight (21 hours), A little raw material was not reacted and the reaction was stopped. The reaction solution was cooled and concentrated to remove xylene. 150 ml of petroleum ether was added to the residue, and a solid precipitated under stirring, followed by filtration to obtain 10.0 g of 3-dimethylamino-1-(3-methoxy-phenyl)-propenone as a reddish-brown oil, 73.2%.

Step 2: Preparation of methyl 6-(3-methoxy-phenyl)-2-methyl-nicotinate 6.1 g of 3-dimethylamino-1-(3-methoxy-phenyl)-propenone (29.3 mmol, 1.0 equiv.), 4.1 g of methyl acetoacetate (35.1 mmol, 1.2 equiv.), 4.52 g of ammonium acetate (58.6 mmol, 2.0 equiv.), 2.2 g of cerium$^{(III)}$ chloride heptahydrate (5.86 mmol, 0.2 equiv.), 879 mg of sodium iodide (5.86 mmol, 0.2 equiv.) and 40 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 6.0 g of methyl 6-(3-methoxy-phenyl)-2-methyl-nicotinate as a brownish yellow liquid, 80.0%.

Step 3: Preparation of methyl 2-bromomethyl-6-(4-methoxy-phenyl)-nicotinate 6.0 g of methyl 6-(3-methoxy-phenyl)-2-methyl-nicotinate (23.3 mmol, 1.0 equiv.), 4.36 g of N-bromosuccinimide (24.5 mmol, 1.05 equiv.), 382.6 mg of azobisisobutyronitrile (2.33 mmol, 0.1 equiv.) and 30 ml of carbon tetrachloride were mixed and refluxed under stirring for 6 hours. The reaction solution was directly subjected to column chromatography, eluting with ethyl acetate/petroleum ether (1:50) to obtain 5.5 g of methyl 2-bromomethyl-6-(4-methoxy-phenyl)-nicotinate as a yellow liquid, 70.5%.

Step 4: Preparation of methyl 2-{[methoxycarbo-nylmethyl-(4-methylphenyl sulfonyl)-amino]-methyl}-6-(3-methoxy-phenyl)-nicotinate 4.0 g of methyl 2-bromomethyl-6-(4-methoxy-phenyl)-nicotinate (11.7 mmol, 1.0 equiv.), 2.69 g of N-p-toluene-sulfonylglycine methyl ester (11.1 mmol, 0.95 equiv.), 3.23 g of potassium carbonate (23.4 mmol, 2.0 equiv.), 160.5 mg of sodium iodide (1.17 mmol, 0.1 equiv.), 10 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 4.8 g of methyl 2-{[methoxycarbonylmethyl-(4-methylphenylsulfonyl)-amino]-methyl}-6-(3-methoxy-phenyl)-nicotinate as a yellow oil, 82.3%.

Step 5: Preparation of methyl 5-hydroxy-2-(3-methoxy-phenyl)-[,7]naphthyridine-6-carboxylate At room temperature, a solution of 4 ml of 30% sodium methoxide in methanol was added dropwise to a solution of 4.8 g (9.64 mmol, 1.0 equiv.) of methyl 2-{[methoxycarbo-nylmethyl-(4-methylphenylsulfonyl)-amino]-methyl}-6-(3-methoxy-phenyl)-nicotinate in 10 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 1.1 mg of methyl 5-hydroxy-2-(3-methoxy-phenyl)-[1,7] naphthy-ridine-6-carboxylate as a pale yellow solid, 36.7%.

Step 6: Preparation of 2-{5-hydroxy-[2-(4-methoxy)-phenyl]-[1,7]-naphthyridine-6-forma-mido} acetic acid 200 mg of methyl 5-hydroxy-2-(3-methoxy-phenyl)-[1,]naphthyridine-6-carboxylate (0.64 mmol, 1.0 equiv.), 167 mg of glycine (2.23 mmol, 3.0 equiv.), a solution of 1.0 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 150 mg of 2-{5-hydroxy-[2-(4-methoxy)-phenyl]-[1,7]-naphthyridine-6-formamido} acetic acid as an off-white solid, 65.8%.

$^1$H NMR (400 MHz, DMSO-d6) δ 13.67 (s, 1H), 12.83 (s, 1H), 9.41-9.49 (m, 1H), 8.89 (s, 1H), 8.73 (d, J=8.8 Hz, 1H), 8.50 (d, J=8.8 Hz, 1H), 7.95-7.88 (m, 1H), 7.53 (t, J=8.0 Hz, 1H), 7.17 (dd, J=8.4, 2.4 Hz, 1H), 4.07 (d, J=6.4 Hz, 2H).

Example 15

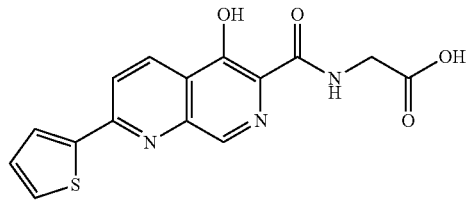 [SMILES: O=C(O)CNC(=O)c1ncc2nc(-c3cccs3)ccc2c1O]

[(5-hydroxy-2-thiophen-2-yl-[1,7]naphthyridine-6-carbonyl)-amino]-acetic acid

Step 1: Preparation of 3-dimethylamino-1-thiophen-2-yl-propenone 12.8 g of 1-acetylthiophen (100.0 mmol, 1.0 equiv.), 35.8 g of N,N-dimethylformamide dimethylacetal (300.0 mmol, 3.0 equiv), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 7.0 g of 3-dimethylamino-1-thiophen-2-yl-propenone as a brownish yellow solid, 38.7%.

Step 2: Preparation of methyl 2-methyl-6-thiophen-2-yl-nicotinate 5.5 g of 3-dimethylamino-1-thiophen-2-yl-propenone (30.0 mmol, 1.0 equiv), 4.10 g of methyl acetoacetate (36.0 mmol, 1.2 equiv.), 4.60 g of ammonium acetate (60.0 mmol, 2.0 equiv.), 2.25 g of cerium$^{(III)}$ chloride heptahydrate (6.0 mmol, 0.2 equiv.), 900 mg of sodium iodide (6.0 mmol, 0.2 equiv.) and 50 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.0 g of methyl 2-methyl-6-thiophen-2-yl-nicotinate as a white solid, 28.6%.

Step 3: Preparation of methyl 2-bromomethyl-6-thiophen-2-yl-nicotinate 2.0 g of methyl 2-methyl-6-thiophen-2-yl-nicotinate (8.7 mmol, 1.0 equiv), 1.63 g of N-bromosuccinimide (9.13 mmol, 1.05 equiv.), 285.7 mg of azobisisobutyronitrile (0.87 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 2.0 g of methyl 2-bromomethyl-6-thiophen-2-yl-nicotinate as a yellow liquid, 74.1%.

Step 4: Preparation of methyl 2-([methoxycarbonyl-methyl-(4-methylphenyl sulfonyl)-amino]-methyl)-6-thiophen-2-yl-nicotinate 2.0 g of methyl 2-bromomethyl-6-thiophen-2-yl-nicoti-nate (6.43 mmol, 1.0 equiv), 1.48 g of N-p-toluenesulfonyl-glycine methyl ester (6.11 mmol, 0.95 equiv.), 1.77 g of potassium carbonate (12.86 mmol, 2.0 equiv.), 96 mg of sodium iodide (0.64 mmol, 0.1 equiv.), 10 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 2 g of methyl 2-{[methoxycarbonylmethyl-(4-methylphenylsulfonyl)-amino]-methyl}-6-thiophen-2-yl-nicotinate as a yellow solid, 65.6%.

Step 5: Preparation of methyl 5-hydroxy-2-thiophen-2-yl-[1,7]naphthyridine-6-carboxylate At room temperature, a solution of 3 ml of 30% sodium methoxide in methanol was added dropwise to a solution of 2.0 g (4.21 mmol, 1.0 equiv.) of methyl 2-{[methoxycarbonylmethyl-(4-methylphenylsulfonyl)-amino]-methyl}-6-thiophen-2-yl-nicotinate in 10 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 1.0 g of methyl 5-hydroxy-2-thiophen-2-yl-[1,7] naphthyridine-6-carboxylate as a yellow solid, 83.3%.

Step 6: Preparation of [(5-hydroxy-2-thiophen-2-yl-[1,7]naphthyridine-6-carbonyl)-amino]-acetic acid 140 mg of methyl 5-hydroxy-2-thiophen-2-yl-[1,7]naphthyridine-6-carboxylate (0.49 mmol, 1.0 equiv.), 110 mg of glycine (1.47 mmol, 3.0 equiv.), a solution of 1.0 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 118 mg of 2[(5-hydroxy-2-thiophen-2-yl-[1,7] naphthyridine-6-carbonyl)-amino]-acetic acid as a yellow-brown solid, 73.0%.

$^1$H NMR (400 MHz, DMSO-d6) δ 13.62 (s, 1H), 12.86 (s, 1H), 9.45-9.42 (m, 1H), 8.85 (s, 1H), 8.64 (d, J=8.8 Hz, 1H), 8.40 (d, J=8.8 Hz, 1H), 8.14 (d, J=4.4 Hz, 1H), 7.83 (d, J=4.8 Hz, 1H), 7.31-7.25 (m, 1H), 4.05 (d, J=6.0 Hz, 2H).

Example 16

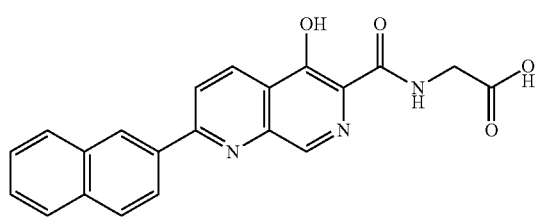 [SMILES: O=C(O)CNC(=O)c1ncc2nc(-c3ccc4ccccc4c3)ccc2c1O]

[(5-hydroxy-2-(naphthalen-2-yl)-[1,7]naphthyridine-6-carbonyl)-amino]-acetic acid (Compound No. 19)

Step 1: Preparation of 3-dimethylamino-1-(naphthalen-2-yl)-propenone 10.0 g of 2-acetylnaphthalene (58.8 mmol, 1.0 equiv.), 21.0 g of N,N-dimethylformamide dimethylacetal (176.2 mmol, 3.0 equiv), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 11.5 g of 3-dimethylamino-1-(naphthalene-2-yl)-propenone as a brownish-yellow solid, 87.1%.

Step 2: Preparation of methyl 2-methyl-6-(naphthalen-2-yl)-nicotinate 5.0 g of 3-dimethylamino-1-(naphthalen-2-yl)-propenone (22.1 mmol, 1.0 equiv), 3.0 g of methyl acetoacetate (26.5 mmol, 1.2 equiv.), 3.4 g of ammonium acetate (44.2 mmol, 2.0 equiva.), 1.65 g of cerium$^{(III)}$ chloride heptahydrate (4.4 mmol, 0.2 equiv.), 660 mg of sodium iodide (4.4 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.0 g of methyl 2-methyl-6-(naphthalen-2-yl)-nicotinate as a yellow solid, 28.6%.

Step 3: Preparation of methyl 2-bromomethyl-6-(naphthalen-2-yl)-nicotinate 2.0 g of methyl 2-methyl-6-(naphthalen-2-yl)-nicotinate (7.2 mmol, 1.0 equiv), 1.35 g of N-bromosuccinimide (7.58 mmol, 1.05 equiv.), 118.2 mg of azobisisobutyronitrile (0.72 mmol, 0.1 equiv.) and 15 ml of carbon tetrachloride were mixed and refluxed under stirring for 6 hours. The reaction solution was directly subjected to column chromatography, eluting with ethyl acetate/petroleum ether (1:50) to obtain 2.0 g of methyl 2-bromomethyl-6-(naphthalen-2-yl)-nicotinate as a yellow liquid, 78.1%.

Step 4: Preparation of methyl 2-{[methoxycarbonylmethyl-(4-methylphenyl sulfonyl)-amino]-methyl}-6-(naphthalen-2-yl)-nicotinate 2.0 g of methyl 2-bromomethyl-6-(naphthalen-2-yl)-nicotinate (5.63 mmol, 1.0 equiv), 1.30 g of N-p-toluenesulfonylglycine methyl ester (5.35 mmol, 0.95 equiv.), 1.55 g of potassium carbonate (11.26 mmol, 2.0 equiv.), 84 mg of sodium iodide (0.56 mmol, 0.1 equiv.), 10 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.0 g of methyl 2-{[methoxycarbonylmethyl-(4-methylphenylsulfonyl)-amino]-methyl}-6-(naphthalen-2-yl)-nicotinate as a yellow solid, 34.2%.

Step 5: Preparation of methyl 5-hydroxy-2-naphthalen-2-yl-[1,7]naphthyridine-6-carboxylate At room temperature, a solution of 1 ml of 30% sodium methoxide in methanol was added dropwise to a solution of 0.8 g (1.54 mmol, 1.0 equiv.) of methyl 2-{[methoxycarbonylmethyl-(4-methylphenylsulfonyl)-amino]-methyl}-6-(naphthalen-2-yl)-nicotinate in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 150 mg of methyl 5-hydroxy-2-(naphthalen-2-yl)-[1,7] naphthyridine-6-carboxylate as a yellow solid, 29.5%.

Step 6: Preparation of [(5-hydroxy-2-(naphthalen-2-yl)-[1,7]naphthyridine-6-carbonyl)-amino]-acetic acid 150 mg of methyl 5-hydroxy-2-naphthalen-2-yl-[1,7]naphthyridine-6-carboxylate (0.45 mmol, 1.0 equiv.), 102 mg of glycine (1.36 mmol, 3.0 equiv.), a solution of 1.0 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 130 mg of 2 [(5-hydroxy-2-(naphthalen-2-yl)-[1,7]naphthyridine-6-carbonyl)-amino]-acetic acid as a yellow-brown solid, 77.2%.

$^1$H NMR (400 MHz, DMSO-d6) δ 13.66 (s, 1H), 9.47-9.41 (m, 1H), 9.02 (br s, 1H), 8.92 (d, J=1.9 Hz, 1H), 8.76 (d, J=8.8 Hz, 1H), 8.64 (d, J=8.8 Hz, 1H), 8.50 (dd, J=8.8, 1.6 Hz, 1H), 8.15-8.08 (m, 2H), 8.05-7.97 (m, 1H), 7.68-7.57 (m, 2H), 4.07 (d, J=6.0 Hz, 2H).

Example 17

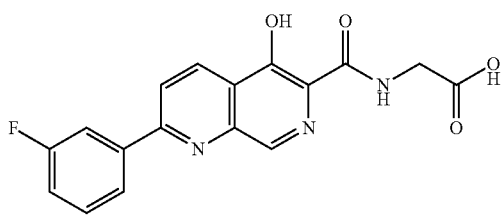 [SMILES: O=C(O)CNC(=O)c1ncc2nc(-c3cccc(F)c3)ccc2c1O]

2-{5-hydroxy-[2-(3-fluoro)-phenyl]-[1,7]-naphthyridine-6-formamido} acetic acid (Compound No. 20)

Step 1: Preparation of 3-dimethylamino-1-(3-fluoro-phenyl)-propenone 10.0 g of 3-fluoroacetophenone (72.4 mmol, 1.0 equiv.), 25.9 g of N,N-dimethylformamide dimethylacetal (217.2 mmol, 3.0 equiv.), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 12.0 g of 3-dimethylamino-1-(3-fluoro-phenyl)-propenone as a brownish-yellow solid, 85.7%.

Step 2: Preparation of methyl 6-(3-fluoro-phenyl)-2-methyl-nicotinate 5.0 g of 3-dimethylamino-1-(3-fluoro-phenyl)-propenone (25.8 mmol, 1.0 equiv.), 3.52 g of methyl acetoacetate (30.9 mmol, 1.2 equiv.), 3.98 g of ammonium acetate (51.6 mmol, 2.0 equiv.), 1.93 g of cerium$^{(III)}$ chloride heptahydrate (5.16 mmol, 0.2 equiv.), 774 mg of sodium iodide (5.16 mmol, 0.2 equiv.) and 30 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 4.8 g of methyl 6-(3-fluoro-phenyl)-2-methyl-nicotinate as a white solid, 75.9%.

Step 3: Preparation of methyl 2-bromomethyl-6-(3-fluoro-phenyl)-nicotinate 4.7 g of methyl 6-(3-fluoro-phenyl)-2-methyl-nicotinate (19.2 mmol, 1.0 equiv.), 3.58 g of N-bromosuccinimide (20.1 mmol, 1.05 equiv.), 315 mg of azobisisobutyronitrile (1.92 mmol, 0.1 equiv.) and 20 ml of carbon tetrachloride were mixed and refluxed under stirring for 6 hours. The reaction solution was directly subjected to column chromatography, eluting with ethyl acetate/petroleum ether (1:50) to obtain 4.5 g of methyl 2-bromomethyl-6-(3-fluoro-phenyl)-nicotinate as a yellow solid, 72.6%.

Step 4: Preparation of methyl 6-(3-fluoro-phenyl)-2-{[methoxycarbonyl methyl-(4-methylphenylsulfonyl)-amino]-methyl}-nicotinate 4.5 g of methyl 2-bromomethyl-6-(3-fluoro-phenyl)-nicotinate (13.9 mmol, 1.0 equiv.), 3.2 g of N-p-toluenesulfonylglycine methyl ester (13.2 mmol, 0.95 equiv.), 3.84 g of potassium carbonate (27.8 mmol, 2.0 equiv.), 208.5 mg of sodium iodide (1.39 mmol, 0.1 equiv.), 15 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 3.5 g of methyl 6-(3-fluoro-phenyl)-2-{[methoxycarbonylmethyl-(4-methylphenylsulfonyl)-amino]-methyl}-nicotinate as a white solid, 51.8%.

Step 5: Preparation of methyl 2-(3-fluoro-phenyl)-5-hydroxy-[1,7]naphthyridine-6-carboxylate At room temperature, a solution of 3 ml of 30% sodium methoxide in methanol was added dropwise to a solution of 2.0 g (4.11 mmol, 1.0 equiv.) of methyl 6-(3-fluoro-phenyl)-2-{[methoxycarbonylmethyl-(4-methylphenylsulfonyl)-amino]-methyl}-nicotinate in 10 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 1.0 g of methyl 2-(3-fluoro-phenyl)-5-hydroxy-[1,7]naphthyridine-6-carboxylate as a pale yellow solid, 82.0%.

Step 6: Preparation of 2-{5-hydroxy-[2-(3-fluoro)-phenyl]-[1,7]-naphthyridine-6-formamido} acetic acid 200 mg of methyl 2-(3-fluoro-phenyl)-5-hydroxy-[1,7]naphthyridine-6-carboxylate (0.67 mmol, 1.0 equiv.), 151 mg of glycine (2.01 mmol, 3.0 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 230 mg of 2-{5-hydroxy-[2-(3-fluoro)-phenyl]-[1,7]-naphthyridine-6-formamido} acetic acid as an yellow brown solid, 89.1%.

$^1$H NMR (400 MHz, DMSO-d6) δ 13.66 (s, 1H), 12.85 (s, 1H), 9.42-9.47 (m, 1H), 8.97 (s, 1H), 8.82-8.68 (m, 2H), 8.62-8.31 (m, 1H), 8.21-8.09 (m, 2H), 7.67-7.60 (m, 1H), 7.44-7.40 (m, 1H), 4.06 (d, J=6.0 Hz, 2H).

Example 18

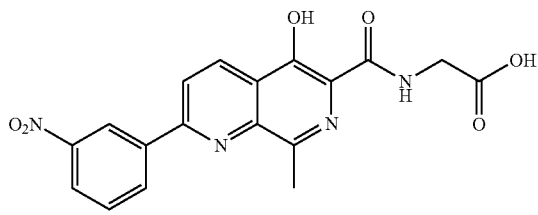 [SMILES: Cc1nc(C(=O)NCC(=O)O)c(O)c2ccc(-c3cccc([N+](=O)[O-])c3)nc12]

2-{5-hydroxy-[2-(3-nitro)-phenyl]-8-methyl-[1,7]-naphthyridine-6-formamido} acetic acid (Compound No. 21)

Step 1: Preparation of 3-dimethylamino-1-(3-nitro-phenyl)-propenone 10 g of 3-nitroacetophenone (60.6 mmol, 1 equiv.), 35.63 g of N,N-dimethylformamide dimethylacetal (181 mmol, 3 equiv.), and 50 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 11.34 g of 3-dimethylamino-1-(3-nitro-phenyl)-propenone as a yellow solid.

Step 2: Preparation of methyl 6-(3-nitro-phenyl)-2-ethyl-nicotinate 6.31 g of 3-dimethylamino-1-(3-nitro-phenyl)-propenone (28.7 mmol, 1 equiv.), 4.47 g of methyl propionylacetate (34.4 mmol, 1.2 equiv.), 4.42 g of ammonium acetate (57.4 mmol, 2.0 equiv.), 2.14 g of cerium$^{(III)}$ chloride heptahydrate (5.7 mmol, 0.2 equiv.), 860 mg of sodium iodide (5.7 mmol, 0.2 equiv.) and 35 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 1.55 g of methyl 6-(3-nitro-phenyl)-2-ethyl-nicotinate as a yellow solid.

Step 3: Preparation of methyl 2-(1-bromoethyl)-6-(3-nitro-phenyl)-nicotinate 1.55 g of methyl 6-(3-nitro-phenyl)-2-ethyl-nicotinate (5.4 mmol, 1 equiv.), 1.16 g of N-bromosuccinimide (6.5 mmol, 1.2 equiv.), 45 mg of azobisisobutyronitrile (0.27 mmol, 0.05 equiv.) and 40 ml of carbon tetrachloride were mixed and refluxed under stirring for 6 hours. The reaction solution was directly subjected to column chromatography, eluting with ethyl acetate/petroleum ether (1:50) to obtain 1.51 g of methyl 2-(1-bromoethyl)-6-(3-nitro-phenyl)-nicotinate as a solid.

Step 4: Preparation of methyl 6-(3-nitro-phenyl)-2-{1-[methoxycarbonyl methyl-(4-methylphenylsulfonyl)-amino]-ethyl}-nicotinate 1.51 g of methyl 2-(1-bromoethyl)-6-(3-nitro-phenyl)-nicotinate (4.1 mmol, 1 equiv.), 996 mg of N-p-toluenesulfonylglycine methyl ester (4.1 mmol, 1 equiv.), 1.2 g of potassium carbonate (8.2 mmol, 2 equiv.), 60 mg of sodium iodide (0.4 mmol, 0.1 equiv.), 30 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 670 mg of methyl 6-(3-nitro-phenyl)-2-{-[methoxycarbonylmethyl-(4-methylphenylsulfonyl)-amino]-ethyl}-nicotinate as a solid.

Step 5: Preparation of methyl 2-(3-nitro-phenyl)-5-hydroxy-8-methyl-[1,7]naphthyridine-6-carboxylate At room temperature, a solution of 30 μl of 30% sodium methoxide in methanol was added dropwise to a solution of 670 mg of methyl 6-(3-nitro-phenyl)-2-{1-[methoxycarbonylmethyl-(4-methylphenylsulfonyl)-amino]-ethyl}-nicotinate in 5 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 280 mg of methyl 2-(3-nitro-phenyl)-5-hydroxy-8-methyl-[1,7]naphthyridine-6-carboxylate as a solid.

Step 6: Preparation of 2-{5-hydroxy-[2-(3-nitro)-phenyl]-8-methyl-[1,7]-naphthyridine-6-formamido} acetic acid 80 mg of methyl 2-(3-nitro-phenyl)-5-hydroxy-8-methyl-[1,7] naphthyridine-6-carboxylate (0.24 mmol, 1 equiv.), 54 mg of glycine (0.72 mmol, 3 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 60 mg of 2-{5-hydroxy-[2-(3-nitro)-phenyl]-8-methyl-[1,7]-naphthyridine-6-formamido} acetic acid as a solid.

¹H NMR (400 MHz, DMSO-d6) δ 13.37 (s, 1H), 9.24 (br s, 1H), 9.12 (t, J=2.0 Hz, 1H), 8.83-8.72 (m, 2H), 8.62 (d, J=8.8 Hz, 1H), 8.43-8.41 (m, 1H), 7.91 (t, J=8.0 Hz, 1H), 4.07 (d, J=6.1 Hz, 2H), 2.98 (s, 3H).

Example 19

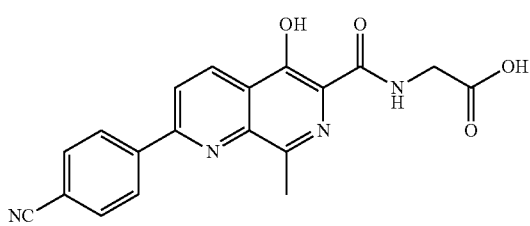 [SMILES: Cc1nc(C(=O)NCC(=O)O)c(O)c2ccc(-c3ccc(C#N)cc3)nc12]

2-{5-hydroxy-[2-(4-cyano)-phenyl]-8-methyl-[1,7]-naphthyridine-6-formamido} acetic acid (Compound No. 22)

Step 1: Preparation of 3-dimethylamino-1-(4-cyano-phenyl)-propenone 14.5 g of 4-acetylbenzonitrile (100 mmol, 1 equiv.), 35.7 g of N,N-dimethylformamide dimethylacetal (300 mmol, 3 equiv.), and 80 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 18.36 g of 3-dimethylamino-1-(4-cyano-phenyl)-propenone as a brown solid.

Step 2: Preparation of methyl 6-(4-cyano-phenyl)-2-ethyl-nicotinate 18.36 g of 3-dimethylamino-1-(4-cyano-phenyl)-propenone (91.8 mmol, 1 equiv.), 11.3 g of methyl propionylacetate (110 mmol, 1.2 equiv.), 14.1 g of ammonium acetate (183 mmol, 2 equiv.), 7.5 g of cerium$^{(III)}$ chloride heptahydrate (20 mmol, 0.2 equiv.), 3 g of sodium iodide (20 mmol, 0.2 equiv.) and 100 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 800 mg of methyl 6-(4-cyano-phenyl)-2-ethyl-nicotinate as a yellow solid.

Step 3: Preparation of methyl 2-(1-bromoethyl)-6-(4-cyano-phenyl)-nicotinate 800 mg of methyl 6-(4-cyano-phenyl)-2-methyl-nicotinate (3 mmol, 1 equiv.), 640 mg of N-bromosuccinimide (3.6 mmol, 1.2 equiv.), 25 mg of azobisisobutyronitrile (0.15 mmol, 0.05 equiv.) and 30 ml of carbon tetrachloride were mixed and refluxed under stirring for 6 hours. The reaction solution was directly subjected to column chromatography, eluting with ethyl acetate/petroleum ether (1:50) to obtain 960 mg of methyl 2-(1-bromoethyl)-6-(4-cyano-phenyl)-nicotinate as a yellow solid.

Step 4: Preparation of methyl 6-(4-cyano-phenyl)-2-{1-[methoxycarbonyl methyl-(4-methylphenylsulfonyl)-amino]-ethyl}-nicotinate 960 mg of methyl 2-(1-bromoethyl)-6-(4-cyano-phenyl)-nicotinate (2.7 mmol, 1 equiv.), 656 mg of N-p-toluenesulfonylglycine methyl ester (2.7 mmol, 1 equiv.), 759 mg of potassium carbonate (5.5 mmol, 2 equiv.), 45 mg of sodium iodide (0.3 mmol, 0.1 equiv.), 20 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 720 mg of methyl 6-(4-cyano-phenyl)-2-{1-[methoxycarbonylmethyl-(4-methylphenylsulfonyl)-amino]-ethyl}-nicotinate as a yellow solid.

Step 5: Preparation of methyl 2-(4-cyano-phenyl)-5-hydroxy-8-methyl-[1,7]naphthyridine-6-carboxylate At room temperature, a solution of 30 μl of 30% sodium methoxide in methanol was added dropwise to a solution of 720 mg of methyl 6-(4-cyano-phenyl)-2-{[methoxycarbonylmethyl-(4-methylphenylsulfonyl)-amino]-methyl}-nicotinate in 6 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 190 mg of methyl 2-(4-cyano-phenyl)-5-hydroxy-8-methyl-[1, 7]naphthyridine-6-carboxylate as a solid.

Step 6: Preparation of 2-{5-hydroxy-[2-(4-cyano)-phenyl]-8-methyl-[1,7]-naphthyridine-6-formamido} acetic acid 64 mg of methyl 2-(4-cyano-phenyl)-5-hydroxy-8-methyl-[1,7]naphthyridine-6-carboxylate (0.2 mmol, 1 equiv.), 45 mg of glycine (0.6 mmol, 3 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 40 mg of 2-{5-hydroxy-[2-(4-cyano)-phenyl]-8-methyl-[1,7]-naphthyridine-6-formamido} acetic acid as a solid.

¹H NMR (400 MHz, DMSO-d6) δ 13.32 (s, 1H), 12.85 (s, 1H), 9.21 (t, J=6.3 Hz, 1H), 8.70 (d, J=8.7 Hz, 1H), 8.53-8.47 (m, 3H), 8.10-8.03 (m, 2H), 4.07 (d, J=6.3 Hz, 2H), 2.94 (s, 3H).

Example 20

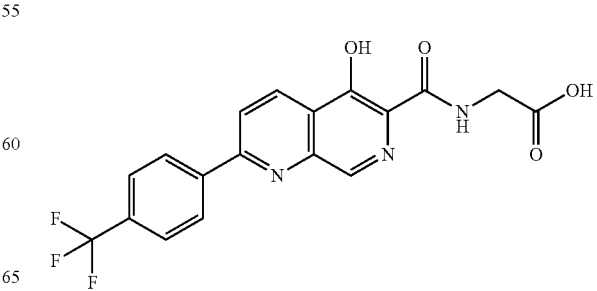

2-{5-hydroxy-[2-(4-trifluoromethyl)-phenyl]-[1,7]-napthyridine-6-formamido} acetic acid (Compound No. 23)

Step 1: Preparation of 3-dimethylamino-1-(4-trifluoromethyl-phenyl)-propenone 15 g of 4-trifluoromethylacetophenone (80 mmol, 1 equiv.), 28.6 g of N,N-dimethylformamide dimethylacetal (240 mmol, 3 equiv.), and 60 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 12.12 g of 3-dimethylamino-1-(4-trifluoromethyl-phenyl)-propenone as a yellow solid.

Step 2: Preparation of methyl 6-(4-trifluoromethyl-phenyl)-2-methyl-nicotinate 12.1 g of 3-dimethylamino-1-(4-trifluoromethyl-phenyl)-propenone (50 mmol, 1.0 equiv.), 8.7 g of methyl acetoacetate (75 mmol, 1.5 equiv.), 7.7 g of ammonium acetate (100 mmol, 2.0 equiv.), 3.75 g of cerium$^{(III)}$ chloride heptahydrate (10 mmol, 0.2 equiv.), 1.5 g of sodium iodide (10 mmol, 0.2 equiv.) and 70 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 12.9 g of methyl 6-(4-trifluoromethyl-phenyl)-2-methyl-nicotinate as a solid.

Step 3: Preparation of methyl 2-bromomethyl-6-(4-trifluoromethyl-phenyl)-nicotinate 12.9 g of methyl 6-(4-trifluoromethyl-phenyl)-2-methyl-nicotinate (43.7 mmol, 1 equiv.), 9.34 g of N-bromosuccinimide (52.5 mmol, 1.2 equiv.), 358 mg of azobisisobutyronitrile (2.2 mmol, 0.05 equiv.) and 50 ml of carbon tetrachloride were mixed and refluxed under stirring for 6 hours. The reaction solution was directly subjected to column chromatography, eluting with ethyl acetate/petroleum ether (1:50) to obtain 14.47 g of methyl 2-bromomethyl-6-(4-trifluoromethyl-phenyl)-nicotinate as an oil.

Step 4: Preparation of methyl 6-(4-trifluoromethyl-phenyl)-2-{[methoxy carbonylmethyl-(4-methylphenylsulfonyl)-amino]-methyl}-nicotinate 14.4 g of methyl 2-bromomethyl-6-(4-trifluoromethyl-phenyl)-nicotinate (38.8 mmol, 1 equiv.), 9.42 g of N-p-toluenesulfonylglycine methyl ester (38.8 mmol, 1 equiv.), 10.7 g of potassium carbonate (77.6 mmol, 2 equiv.), 578 mg of sodium iodide (3.9 mmol, 0.1 equiv.), 100 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 7.87 g of methyl 6-(4-trifluoromethyl-phenyl)-2-{[methoxycarbonylmethyl-(4-methylphenylsulfonyl)-amino]-methyl}-nicotinate as an oil.

Step 5: Preparation of methyl 2-(4-trifluoromethyl-phenyl)-5-hydroxy-[1, 7] naphthyridine-6-carboxylate At room temperature, a solution of 5 ml of 30% sodium methoxide in methanol was added dropwise to a solution of 7.87 g of methyl 6-(4-trifluoromethyl-phenyl)-2-{[methoxycarbonylmethyl-(4-methylphenylsulfonyl)-amino]-methyl}-nicotinate in 50 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 1.23 g of methyl 2-(4-trifluoromethyl-phenyl)-5-hydroxy-[1,7]naphthyridine-6-carboxylate as a yellow solid.

Step 6: Preparation of 2-{5-hydroxy-[2-(4-trifluoromethyl)-phenyl]-[1,7]-naphthyridine-6-formamido} acetic acid 200 mg of methyl 2-(4-trifluoromethyl-phenyl)-5-hydroxy-[1,7]naphthyridine-6-carboxylate (0.58 mmol, 1 equiv.), 130 mg of glycine (1.73 mmol, 3 equiv.), a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 120 mg of 2-{5-hydroxy-[2-(4-trifluoromethyl)-phenyl]-[1,7]-naphthyridine-6-formamido}acetic acid as a solid.

$^1$H NMR (400 MHz, DMSO-d6) δ 13.61 (s, 1H), 12.94 (s, 1H), 9.44 (d, J=6.6 Hz, 1H), 8.98 (s, 1H), 8.75 (d, J=8.7 Hz, 1H), 8.56-8.52 (m, 3H), 7.95 (d, J=8.1 Hz, 2H), 4.06 (d, J=6.6 Hz, 2H).

Example 21

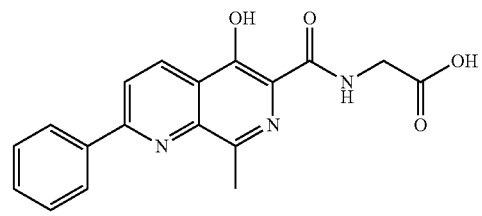

2-{5-hydroxy-8-methyl-[2-phenyl]-[1,7]-naphthyridine-6-formamido} acetic acid (Compound No. 24)

Step 1: Preparation of 3-dimethylamino-1-phenyl-propenone 5 g of acetophenone, 15 g of N,N-dimethylformamide dimethylacetal, and 60 ml of xylene were refluxed overnight (21 hours), a little raw material was not reacted and the reaction was stopped. The reaction solution was cooled and concentrated to remove xylene. 150 ml of petroleum ether was added to the residue, and a solid precipitated under stirring, followed by filtration to obtain 4.5 g of 3-dimethylamino-1-phenyl-propenone as a yellow solid, 62%.

Step 2: Preparation of methyl 6-phenyl-2-ethyl-nicotinate 4.2 g of 3-dimethylamino-1-phenyl-propenone, 4.68 g of methyl acetoacetate, 4.29 g of ammonium acetate, 1.97 g of cerium$^{(III)}$ chloride heptahydrate, 1.0 g of sodium iodide and 50 ml of isopropanol were mixed and refluxed overnight under stirring. The reaction solution was cooled and filtered, and the filtrate was concentrated and subjected to column chromatography, eluting with ethyl acetate/petroleum ether (1:50) to obtain 2.97 g of methyl 6-phenyl-2-ethyl-nicotinate as a solid, 71%.

Step 3: Preparation of methyl 2-(1-bromoethyl)-6-phenyl-nicotinate 2.9 g of methyl 6-phenyl-2-ethyl-nicotinate, 2 g of N-bromosuccinimide, 1 g of azobisisobutyronitrile and 100 ml of carbon tetrachloride were mixed and refluxed under stirring for 6 hours. The reaction solution was filtered to remove insoluble matters and then concentrated, which was directly used in step 4.

Step 4: Preparation of methyl 6-phenyl-2-{1-[methoxycarbonylmethyl-(4-methylphenylsulfonyl)-amino]-ethyl}-nicotinate The crude product of methyl 2-(1-bromoethyl)-6-phenyl-nicotinate, 2.6 g of N-p-toluenesulfonylglycine methyl ester, 4.0 g of potassium carbonate, 320 mg of sodium iodide, 100 ml of N,N-dimethylformamide were mixed and reacted at 50° C. for 8 hours. The reaction solution was diluted with 10 ml of water and extracted with 60 ml of ethyl acetate in three parts. The organic layer was concentrated to obtain a residue, which was subjected to column chromatography, eluting with ethyl acetate/petroleum ether (1:10-1:1) to obtain 1.0 g of methyl 6-phenyl-2-{1-[methoxycarbonylmethyl-(4-methylphenylsulfonyl)-amino]-ethyl}-nicotinate.

Step 5: Preparation of methyl 2-phenyl-5-hydroxy-8-methyl-[1,7]naphthyridine-6-carboxylate At room temperature, a solution of 2 ml of 5 mol/L sodium methoxide in methanol was added dropwise to a solution of 1 g of methyl 6-phenyl-2-{1-[methoxycarbonyl-methyl-(4-methylphenylsulfonyl)-amino]-methyl}-nicotinate in 50 ml of DMSO, and reacted at room temperature until the reaction was completed. 1 mol/L dilute hydrochloric acid was added dropwise to the reaction solution until the pH reached 3-4. The reaction solution was extracted with ethyl acetate (30 ml) in three parts. The ethyl acetate layer was concentrated and the residue was subjected to column chromatography, eluting with ethyl acetate/dichloromethane (1:10) to obtain 500 mg of methyl 2-phenyl-5-hydroxy-8-methyl-[1,7]naphthyridine-6-carboxylate as a yellow solid.

Step 6: Preparation of 2-{5-hydroxy-2-phenyl-8-methyl-[1,7]-naphthyridine-6-formamido} acetic acid 200 mg of methyl 2-phenyl-5-hydroxy-8-methyl-[1,7]naphthyridine-6-carboxylate, 209 mg of glycine, a solution of 0.5 ml of 5 mol/L sodium methoxide in methanol, and methanol (5 ml) were mixed and sealed in a closed reactor at 120° C. for 24 hours. Then the reaction solution was cooled, adjusted to acidic pH with 1 mol/L hydrochloric acid to precipitate and filtered. The filter cake was washed with a small amount of water and methanol, and the filter cake was dried to obtain 30 mg of 2-{5-hydroxy-2-phenyl-8-methyl-[1,7]-naphthyridine-6-formamido} acetic acid as a solid.

1H NMR (400 MHz, DMSO-d6) δ 13.36 (s, 1H), 9.22 (br s, 1H), 8.71 (d, J=8.8 Hz, 1H), 8.48 (d, J=8.8 Hz, 1H), 8.41-8.33 (m, 2H), 7.67-7.53 (m, 3H), 4.06 (d, J=6.1 Hz, 2H), 2.98 (s, 3H).

Biological Example 1: Development and Screening of In Vitro Detection Methods: Promotion of Erythropoietin Expression in Hepatoma Cells Hep3B In Vitro by HIF-PHD2 Inhibitor Compounds The complete medium for culture of Experimental hepatoma cells Hep3B (China Center for Type Culture Collection, CCTCC) was MEM (Cat# GNM 41500, GIBCO, provided by Hangzhou Genom Biopharmaceutical Technology Co., Ltd) supplemented with 10% serum FBS (Cat#10099-141, GIBCO) and 1% P/S (Cat#GNM15140, provided by Hangzhou Genom Biopharmaceutical Technology Co., Ltd). Cells were cultured in a 37° C., 5% $CO_2$ incubator. Experimental reagents included dimethyl sulfoxide (for molecular biology, >=99.9%, Catalog # D8418) purchased from Sigma. The ELISA kit was purchased from Quantikine IVD ELISA, Human Erythropoietin (R&D, DEP00). The test control AKB-6548 was prepared by the inventors or obtained by commercial purchase. The test substance was stored at −20° C. in the dark.

The test substance and the positive control substance were fully dissolved in sterile water or dimethylsulfoxide under dark conditions and prepared into a stock solution at a concentration of $10^{-1}$ mol/L or $10^{-2}$ mol/L. Each of the stock solutions was stored at −20° C. MEM medium containing 0.5% FBS was used as a diluent to dilute the stock solution of the test substance, to prepare a diluted test substance at a concentration of 100 μmol/L and 10 μmol/L. To a 96-well culture plate was added 200 μl/well (1.5 or 2.0×$10^4$ cells/well) of hepatoma cells Hep3B complete medium suspension and incubated overnight at 37° C. in a 5% $CO_2$ incubator. The solution in the 96-well culture plate was removed and the cells were washed once with the MEM medium containing 0.5% FBS. 200 μl/well of the test substance was added in the dark, at a dose of 100 μmol/L and 10 μmol/L, and each dose set 2 wells, a test well and a spare well. A cell control well was prepared by replacing the test solution with the diluent (without test substance and solvent). A solvent control well was prepared by replacing the test solution with the diluent containing the corresponding concentration of solvent (dimethylsulfoxide) (without test substance). They were cultured in a 5% $CO_2$ incubator at 37° C. for 24 hours. The supernatant was absorbed as a sample and cryopreserved at −20° C. for use. 100 μl/well of stop solution was added. OD value was detected by microplate reader A450 nm-A600 nm. The expression level of EPO (mIU/mL) promoted by the test substance was obtained according to the standard curve. The test results are shown in the following table:

TABLE 1

Promotion of EPO expression level by test substances (mIU/mL)

| Compound No. | EPO level of the test substance (mIU/mL) |
|---|---|
| AKB-6548 (positive control) | 0.13 |

TABLE 1-continued

Promotion of EPO expression level by test substances (mIU/mL)

| Compound No. | EPO level of the test substance (mIU/mL) |
|---|---|
| FG-4592 (positive control) | 0.378 |
| 1 | 0.71 |
| 2 | 0.64 |
| 3 | 0.52 |
| 4 | 1.512 |
| 5 | 1.89 |
| 6 | 2.268 |
| 8 | 0.68 |
| 9 | 0.60 |
| 10 | 0.64 |
| 11 | 4.158 |
| 12 | 4.536 |
| 13 | 0.832 |
| 14 | 5.435 |
| 15 | 6.316 |
| 16 | 7.046 |
| 17 | 7.757 |
| 18 | 8.888 |
| 19 | 9.786 |
| 20 | 10.685 |
| 21 | 0.325 |
| 22 | 0.53 |
| 23 | 0.72 |
| 24 | 0.44 |

The biological activity test results show that compared to the positive control FG-4592, the compounds of the present invention have a more significant promotion effect on intracellular EPO expression, and most of the intracellular EPO levels reach more than 1.5 times of that of the positive control FG-4592.

Biological Example 2: Detection of Inhibitory Effect of the Compounds of the Invention on PHD ($IC_{50}$)

The interaction between hypoxia-inducible factor HIF-1α and VBC complex (von Hippel-Lindau protein-Elongin B-Elongin C, VBC) was detected by Fluorescence polarization (FP) method, to measure the enzyme inhibitory activity of the HIF Prolyl hydroxylases 2 (PHD2) inhibitor compounds.

To a NETN (20 mM Tris.HCl, 100 mM NaCl, 1 mM EDTA, 0.5% NP-40, 1 mM PMSF) buffer containing 200 μM ascorbic acid, 20 μM α-ketoglutaric acid, 100 μM $FeCl_2$ was added FAM-HIF (556-575) at a final concentration of 1 μM in the dark. Subsequently, the desired concentration of the test compound or the positive compound was added (the compound was replaced by the buffer in the negative control and the positive control). Finally, PHD2 was added at a final concentration of 0.5 μg/μl (PHD2 was replaced by the buffer in the negative control). They were mixed well and allowed to stand at room temperature for 30 minutes in the dark followed by 95° C. water bath for 1 minute, and then the reaction was terminated. After the temperature drops to room temperature, the sample was prepared well for use. EBC buffer (50 mM Tris.HCl, 120 mM NaCl, 0.5% NP-40) was added to the corresponding wells of a black 96-well test plate. A GST-VBC complex was added to the corresponding test wells at a final concentration of 300 nM (using the wells containing only EBC buffer as blank wells). Subsequently, the corresponding PHD2 prolyl hydroxylation reaction sample was added in the dark as a substrate with a final concentration of 100 nM. After mixing well, the lateral and longitudinal fluorescence intensity values were measured using a full-wavelength multifunctional microplate reader (TECAN infinite M1000) at an excitation wavelength of 407 nm and an emission wavelength of 518 nm.

The fluorescence polarization (mP) was calculated:

$$mP = 1000 \times (\text{lateral value} - G\text{ factor} \times \text{longitudinal value})/(\text{lateral value} + G\text{ factor} \times \text{longitudinal value})$$

wherein, lateral value=lateral fluorescence intensity value of test well−lateral fluorescence intensity value of blank well, longitudinal value=longitudinal fluorescence intensity value of test well−longitudinal fluorescence intensity value of blank well, PHD2 inhibition rate (%) of the test compound was calculated according to the following formula:

$$\text{Inhibition rate (\%)} = 1 - (mP \text{ test well} - mP \text{ negative control well})/(mP \text{ positive control well} - mP \text{ negative control well}).$$

The $IC_{50}$ was calculated using the non-linear regression data analysis method of Graphpad Prism 4.0 software (Golden software, Golden, Colo., USA). The results show that the compounds of the present invention have significant inhibitory effect on HIF prolyl hydroxylase.

TABLE 2

Inhibitory effect of test substances on PHD

| Compound No. | IC50 (μM) |
|---|---|
| AKB-6548 (positive control) | 68 |
| FG-4592 (positive control) | 190 |
| 1 | 18 |
| 2 | 11 |
| 3 | 85 |
| 4 | 6.9 |
| 5 | 1.7 |
| 6 | 0.41 |
| 8 | 43 |
| 9 | 84 |
| 10 | 63 |
| 11 | 39 |
| 12 | 4.1 |
| 13 | 0.41 |
| 14 | 10 |
| 15 | 7.7 |
| 16 | 48 |
| 17 | 20 |
| 18 | 5.7 |
| 19 | 7.5 |
| 20 | 0.82 |
| 21 | 14 |
| 22 | 9.3 |
| 23 | 5.2 |
| 24 | 0.44 |

Biological Example 3: Effect of the Compounds of the Present Invention on Increasing Erythrocyte of Normal Mice 80 male Balb/c mice were divided into 11 groups, with 8 animals for each drug group, 10 animals for blank control group. Drug group: AKB-6548, 100 mg/kg, oral administration, once a day×3; FG-4592, 25 mg/kg, oral administration, once a day×3; EPO, 100 IU/kg, Day 1 and Day 3, subcutaneous injection, as positive control groups. Each of the compounds of the present invention was orally administrated at 25 mg/kg, once a day×3. Four hours after the last administration, orbital blood of all animals were collected and treated with EDTA-K2 anticoagulant, and reticulocytes (RETIC) were counted with a blood cell automated analyzer. The results show that the counts of the control compounds and the compounds of the present invention are higher than those of the normal animals (p<0.01).

| Mice No. # | Excipient Control | Four hours after the last administration AKB-6548-A (100 mg/kg) Oral, once a day × 3 | RETIC FG-4592-A (25 mg/kg) Oral, once a day × 3 | EPO (100 IU/kg) Subcutaneous injection, Day 1 and Day 3 | 14 (25 mg/kg) Oral, once a day × 3 | 6 (25 mg/kg) Oral, once a day × 3 | 15 (25 mg/kg) Oral, once a day × 3 | 23 (25 mg/kg) Oral, once a day × 3 |
|---|---|---|---|---|---|---|---|---|
| 1 | 3.2 | 4.2 | 4 | 4.3 | 4 | 3.9 | 3.8 | 9.1 |
| 2 | 2.6 | 5.3 | 3.4 | 5.1 | 4 | 5.4 | 3.1 | 3.2 |
| 3 | 3.3 | 5.3 | 3.6 | 5 | 4 | 5.2 | 4.9 | 2.9 |
| 4 | 3.3 | 6.1 | 3.8 | 5.9 | 3.8 | 5.2 | 4.6 | 3.2 |
| 5 | 4.1 | 4 | 3.8 | 2.5 | 4.1 | 4.8 | 4.9 | 3.2 |
| 6 | 1.5 | 4.2 | 4 | 2.2 | 5.8 | 6.3 | 4.9 | 3 |
| 7 | 2.3 | 4 | 3.5 | 2.6 | 3.4 | 4.7 | 4.1 | 5.1 |
| 8 | 1.4 | 4.9 | 4.4 | 2.2 | 4.3 | 6.4 | 3.7 | |
| 9 | 2.4 | | | | | | | |
| 10 | 1.8 | | | | | | | |
| Average | 2.68 | 4.75 | 3.73 | 3.73 | 4.18 | 5.24 | 4.25 | 4.24 |
| SD | 0.89 | 0.77 | 0.24 | 1.51 | 0.71 | 0.83 | 0.68 | 2.27 |
| p1, in comparison with control | | 0.0001 | 0.0019 | 0.0633 | 0.0008 | 0.0000 | 0.0005 | 0.0522 |
| p2, in comparison with AKB | | | 0.0069 | 0.1098 | 0.1427 | 0.2430 | 0.1912 | 0.5613 |
| p3, in comparison with FG | | | | 0.8751 | 0.2080 | 0.0005 | 0.1226 | 0.6032 |
| p4, in comparison with EPO | | | | | 0.4583 | 0.0263 | 0.3855 | 0.6073 |

What is claimed is:

1. A compound having the following formula (I) or a pharmaceutically acceptable salt thereof:

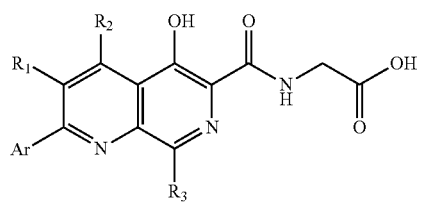

(I)

wherein,
$R_1$, $R_2$ are each independently hydrogen;
$R_3$ is hydrogen or $C_{1-3}$ alkyl;
Ar is an aromatic ring or an aromatic heterocyclic ring selected from the group consisting of a naphthalene ring, a pyridine ring, a thiophene ring, a furan ring and a substituted benzene ring;
wherein the substituted benzene ring has the following structure:

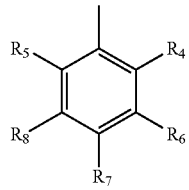

wherein $R_4$, $R_5$, $R_6$, $R_7$ and $R_8$ are independently selected from hydrogen, halogen, hydroxy, nitro, cyano and phenyl, $C_{1-7}$ alkyl, $C_{1-3}$ alkoxy, $C_{1-3}$ alkoxy optionally substituted by halogen, $C_{1-3}$ alkyl optionally substituted by halogen.

2. The compound of claim 1 or a pharmaceutically acceptable salt thereof, wherein the pharmaceutically acceptable salt is a base addition salt.

3. The compound of claim 1 or a pharmaceutically acceptable salt thereof, wherein the compound has the following formula (II):

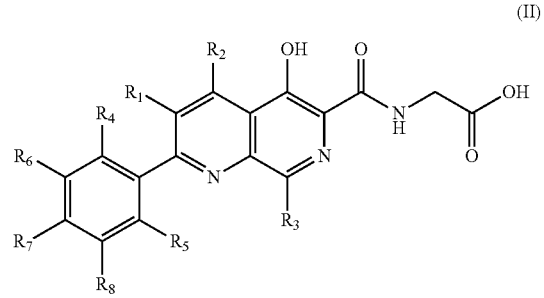

(II)

wherein $R_4$, $R_5$, $R_6$, $R_7$ and $R_8$ are independently selected from hydrogen, halogen, hydroxy, nitro, cyano and phenyl, $C_{1-7}$ alkyl, $C_{1-3}$ alkoxy, $C_{1-3}$ alkoxy optionally substituted by halogen, $C_{1-3}$ alkyl optionally substituted by halogen.

4. The compound of claim 1 or a pharmaceutically acceptable salt thereof, wherein the compound is selected from the group consisting of:

| No. | Structure |
|---|---|
| 1 | 2-phenyl-4-hydroxy-1,7-naphthyridine-6-carboxamide-N-glycine |
| 2 | 2-(4-methoxyphenyl)-4-hydroxy-1,7-naphthyridine-6-carboxamide-N-glycine |
| 3 | 2-(4-chlorophenyl)-8-methyl-4-hydroxy-1,7-naphthyridine-6-carboxamide-N-glycine |
| 4 | 2-(3-methoxyphenyl)-8-methyl-4-hydroxy-1,7-naphthyridine-6-carboxamide-N-glycine |
| 5 | 2-(pyridin-3-yl)-8-methyl-4-hydroxy-1,7-naphthyridine-6-carboxamide-N-glycine |
| 6 | 2-(3-chlorophenyl)-4-hydroxy-1,7-naphthyridine-6-carboxamide-N-glycine |
| 7 | 2-(3-chlorophenyl)-8-methyl-4-hydroxy-1,7-naphthyridine-6-carboxamide-N-glycine |
| 8 | 2-(4-chlorophenyl)-4-hydroxy-1,7-naphthyridine-6-carboxamide-N-glycine |
| 9 | 2-phenyl-8-methyl-4-hydroxy-1,7-naphthyridine-6-carboxamide-N-glycine |
| 10 | 2-(4-methoxyphenyl)-8-methyl-4-hydroxy-1,7-naphthyridine-6-carboxamide-N-glycine |
| 11 | 2-(4-tert-butylphenyl)-8-methyl-4-hydroxy-1,7-naphthyridine-6-carboxamide-N-glycine |
| 12 | 2-(3-bromophenyl)-8-methyl-4-hydroxy-1,7-naphthyridine-6-carboxamide-N-glycine |
| 13 | 2-(3-bromophenyl)-4-hydroxy-1,7-naphthyridine-6-carboxamide-N-glycine |
| 14 | 2-(naphthalen-1-yl)-4-hydroxy-1,7-naphthyridine-6-carboxamide-N-glycine |
| 15 | 2-(3-methoxyphenyl)-4-hydroxy-1,7-naphthyridine-6-carboxamide-N-glycine |
| 16 | 2-(4-tert-butylphenyl)-4-hydroxy-1,7-naphthyridine-6-carboxamide-N-glycine |

| No. | Structure |
|---|---|
| 17 | 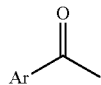 |
| 18 | 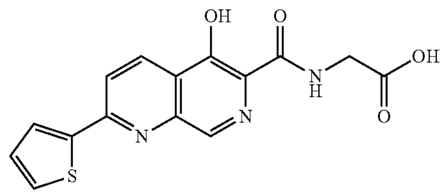 [SMILES: O=C(O)CNC(=O)c1ncc2nc(-c3cccs3)ccc2c1O] |
| 19 | 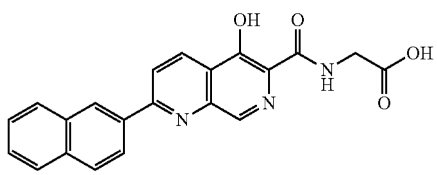 [SMILES: O=C(O)CNC(=O)c1ncc2nc(-c3ccc4ccccc4c3)ccc2c1O] |
| 20 | 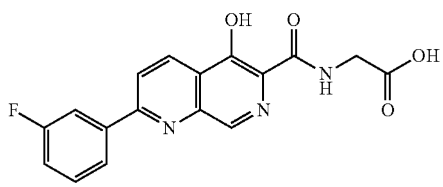 [SMILES: O=C(O)CNC(=O)c1ncc2nc(-c3cccc(F)c3)ccc2c1O] |
| 21 | 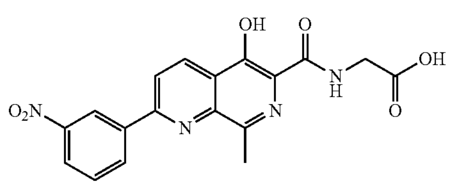 [SMILES: Cc1nc(C(=O)NCC(=O)O)c(O)c2ccc(-c3cccc([N+](=O)[O-])c3)nc12] |
| 22 | 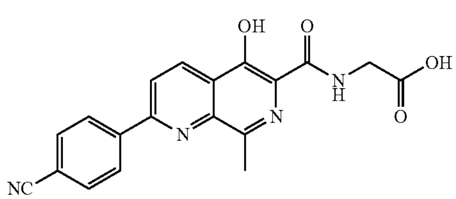 [SMILES: Cc1nc(C(=O)NCC(=O)O)c(O)c2ccc(-c3ccc(C#N)cc3)nc12] |
| 23 | 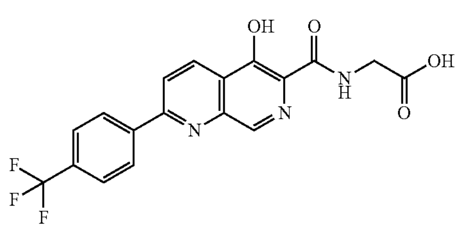 [SMILES: O=C(O)CNC(=O)c1ncc2nc(-c3ccc(C(F)(F)F)cc3)ccc2c1O] |
| 24 | 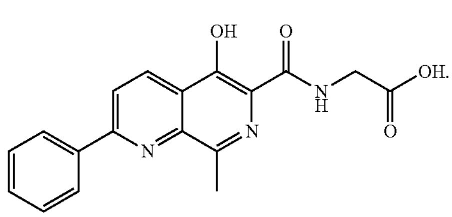 [SMILES: Cc1nc(C(=O)NCC(=O)O)c(O)c2ccc(-c3ccccc3)nc12] |

5. A method for preparing the compound of claim 1, comprising:

step 1: subjecting the compound of the following formula

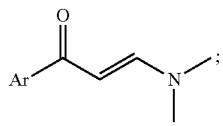

and N, N-dimethylformamide dimethylacetal under reflux to condensation reaction, to form a compound of formula (III)

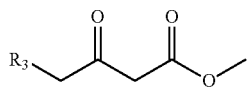

step 2: in the presence of an ammonium salt, a catalyst and a solvent, subjecting the intermediate (III) obtained in step 1 and an $R_3$-substituted methyl acylacetate having the following formula

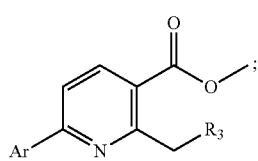

to condensation reaction, to form an intermediate (IV)

IV

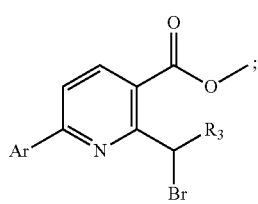

step 3: in the presence of a bromination reaction initiator and a solvent, subjecting the methyl or methylene group in the intermediate (IV) obtained in the step 2 to bromination reaction, to form a bromide intermediate (V)

V step 4: under the catalysis of a base and in the presence of a solvent, replacing the intermediate (V) obtained in the step 3 with toluenesulfonylglycine methyl ester, to form a p-toluenesulfonyl intermediate (VI)

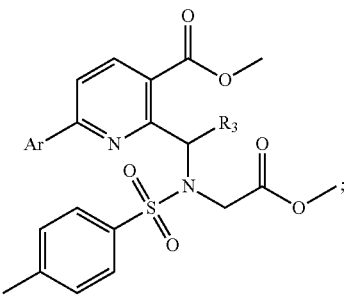

step 5: subjecting the intermediate (VI) obtained in the step 4 to cyclization reaction under basic conditions, to form a methyl 5-hydroxy-1,7-naphtholidinate intermediate (VII)

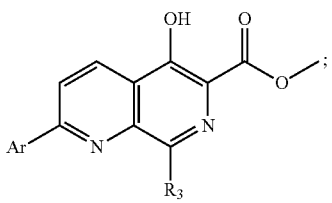

step 6: subjecting the intermediate (VII) obtained in the step 5 and glycine to replacement reaction under basic conditions in a confined heating environment, to directly form the compound of formula (I);

wherein, $R_3$ and Ar are as defined in claim 1.

6. The method of claim 5, wherein in the step 1, a solvent selected from the group consisting of toluene and xylene is used; in the step 2, the ammonium salt is selected from the group consisting of ammonium carbonate, ammonium bicarbonate, ammonium chloride, and ammonium acetate; the catalyst is selected from the group consisting of cerium$^{(III)}$ chloride, SnCl$_4$, TiCl$_4$, ZnCl$_2$, AlCl$_3$, and boron trifluoride etherate; the solvent is selected from the group consisting of ethanol, methanol, isopropanol, and t-butanol; in the step 3, the brominating reagent is selected from the group consisting of N-bromosuccinimide, dibromohydantoin, cuprous $^{(II)}$bromide, and liquid bromine; the bromination reaction initiator is selected from the group consisting of azobisisonitrile, and benzoyl peroxide; the bromination reaction solvent is selected from the group consisting of carbon tetrachloride, dichloromethane and chloroform; in the step 4, the base is selected from the group consisting of potassium carbonate, cesium carbonate, and sodium carbonate; the reaction solvent is selected from the group consisting of N, N-dimethylformamide, N-methylpyrrolidone, N, N-dimethylacetamide, or dimethylsulfoxide; the reaction temperature is 20~80° C.; in the step 5, the base is selected from the group consisting of sodium methoxide, sodium ethoxide, potassium tert-butoxide, and sodium tert-butoxide; the reaction solvent is selected from the group consisting of N, N-dimethylformamide, N-methylpyrrolidone, N, N-dimethylacetamide, dimethyl sulfoxide, methanol, ethanol, and tetrahydrofuran; the reaction temperature is 0~40° C.; and the reaction time is 0.5~3 hours; in the step 6, the base is selected from the group consisting of sodium methoxide, sodium ethoxide, potassium tert-butoxide, or sodium tert-butoxide; the reaction solvent is selected from the group consisting of methanol, ethanol, isopropanol, and n-butanol, the reaction temperature is 80~140° C.

7. A pharmaceutical composition, comprising a compound of claim 1 or a pharmaceutically acceptable salt thereof, and a pharmaceutically acceptable carrier.

8. A method for inhibiting HIF prolyl hydroxylase, the method comprising administering the pharmaceutical composition of claim 7.

9. A method for promoting the generation of endogenous EPO, the method comprising administering the pharmaceutical composition of claim 7.

10. A method for stabilizing hypoxia-inducible factor α, the method comprising administering the pharmaceutical composition of claim 7.

11. A method for treating chronic disease-related anemia in a subject, the method comprising administering to the subject the pharmaceutical composition of claim 7.

12. The method of claim 11, wherein the chronic disease-related anemia is selected from the group consisting of rheumatoid arthritis, rheumatism and inflammatory bowel disease.

13. A method for increasing the production of inflammatory cytokines in a subject, the method comprising administering to the subject the pharmaceutical composition of claim 7.

14. The method of claim 13, wherein the inflammatory cytokines include tumor necrosis factor, interleukin and interferon.

15. A method for treating anemia in a subject resistant to the treatment of exogenous administration of erythropoietin, the method comprising administering to the subject the pharmaceutical composition of claim 7, wherein the pharmaceutical composition enhances the response of hematopoietic precursor cells to the erythropoietin.

16. A method for increasing the production of a factor required for iron ingestion, iron transport and iron utilization in a subject, wherein the factor is selected from the group consisting of erythrocyte aminolevulinic acid synthase, transferrin, transferrin receptor and plasma ceruloplasmin, the method comprising administering to the subject the pharmaceutical composition of claim 7.

17. A method for inhibiting HIF prolyl hydroxylase in a subject, comprising administering to the subject a compound of claim 1 or a pharmaceutically acceptable salt thereof.

18. A method for promoting the generation of endogenous EPO in a subject, comprising administering to the subject a compound of claim 1 or a pharmaceutically acceptable salt thereof.

19. A method for stabilizing hypoxia-inducible factor α in a subject, comprising administering to the subject a compound of claim 1 or a pharmaceutically acceptable salt thereof.

20. A method for treating chronic disease-related anemia in a subject, comprising administering to the subject a compound of claim 1 or a pharmaceutically acceptable salt thereof.

21. The method of claim 20, wherein the chronic disease-related anemia is selected from the group consisting of rheumatoid arthritis, rheumatism and inflammatory bowel disease.

22. A method for increasing the production of inflammatory cytokines in a subject, comprising administering to the subject a compound of claim 1 or a pharmaceutically acceptable salt thereof.

23. The method of claim 22, wherein the inflammatory cytokines include tumor necrosis factor, interleukin and interferon.

24. A method for treating anemia in a subject that is resistant to the treatment of exogenous administration of erythropoietin, comprising administering to the subject a compound of claim 1 or a pharmaceutically acceptable salt thereof, wherein the compound enhances the response of hematopoietic precursor cells to the erythropoietin.

25. A method for increasing the production of a factor required for iron ingestion, iron transport and iron utilization in a subject, comprising administering to the subject a compound of claim 1 or a pharmaceutically acceptable salt thereof, wherein the factor is selected from the group consisting of erythrocyte aminolevulinic acid synthase, transferrin, transferrin receptor and plasma ceruloplasmin.

\* \* \* \* \*